United States Patent
Erikson et al.

(10) Patent No.: US 6,325,757 B1
(45) Date of Patent: Dec. 4, 2001

(54) DIV: ULTRASONIC CAMERA

(75) Inventors: Kenneth R. Erikson, Watertown; Timothy E. White, Acton; R. Calvin Owen, Jr., North Chelmsford; Anthony M. Nicoli, Pepperell; Neal R. Butler, Acton, all of MA (US)

(73) Assignee: ASIS

( * ) Notice: Subject to any disclaimer, the term of this patent is extended or adjusted under 35 U.S.C. 154(b) by 0 days.

(21) Appl. No.: 09/636,343

(22) Filed: Aug. 10, 2000

Related U.S. Application Data

(60) Division of application No. 09/050,224, filed on Mar. 28, 1998, which is a continuation-in-part of application No. 08/621,104, filed on Mar. 22, 1996, now Pat. No. 5,732,706.

(51) Int. Cl.[7] ........................................ A61B 8/00
(52) U.S. Cl. ................................. 600/437; 600/459
(58) Field of Search .................... 600/437, 459, 600/460, 443, 447, 438

(56) References Cited

U.S. PATENT DOCUMENTS

| | | | |
|---|---|---|---|
| 4,092,867 | 6/1978 | Matzuk | 73/609 |
| 4,409,839 | 10/1983 | Taenzer . | |
| 4,459,853 | * 7/1984 | Miwa et al. | 600/437 |
| 4,581,936 | * 4/1986 | Granz et al. | 73/599 |
| 5,483,963 | 1/1996 | Butler et al. | 600/447 |
| 5,715,826 | 2/1998 | Horrocks et al. . | |

* cited by examiner

*Primary Examiner*—Marvin M. Lateef
*Assistant Examiner*—Maulin Patel
(74) *Attorney, Agent, or Firm*—Moffa & Sun, P.A.

(57) ABSTRACT

An ultrasonic camera having a high efficiency ultrasonic lens is coupled to a ultrasonic transmitter/receiver by a stretched membrane interface. The ultrasonic lens provides highly efficient transmission of ultrasound without introducing aberrations. The ultrasound system also uses a quasi incoherent source to reduce speckle noise in the image.

22 Claims, 22 Drawing Sheets

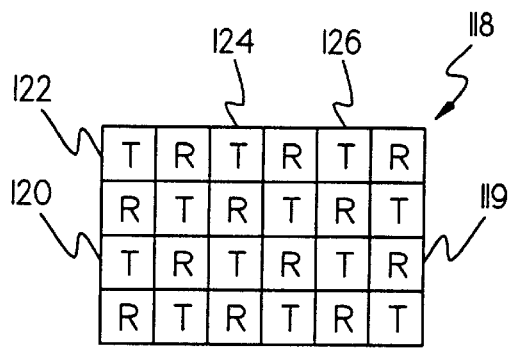
*Fig- 4*
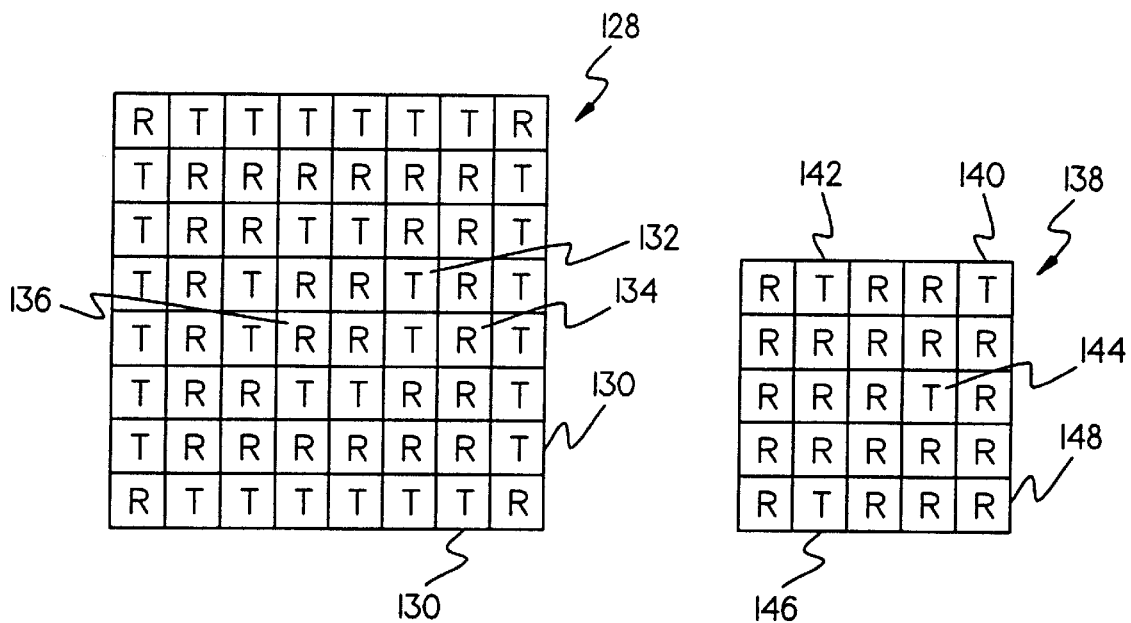
*Fig- 5*  *Fig- 6*

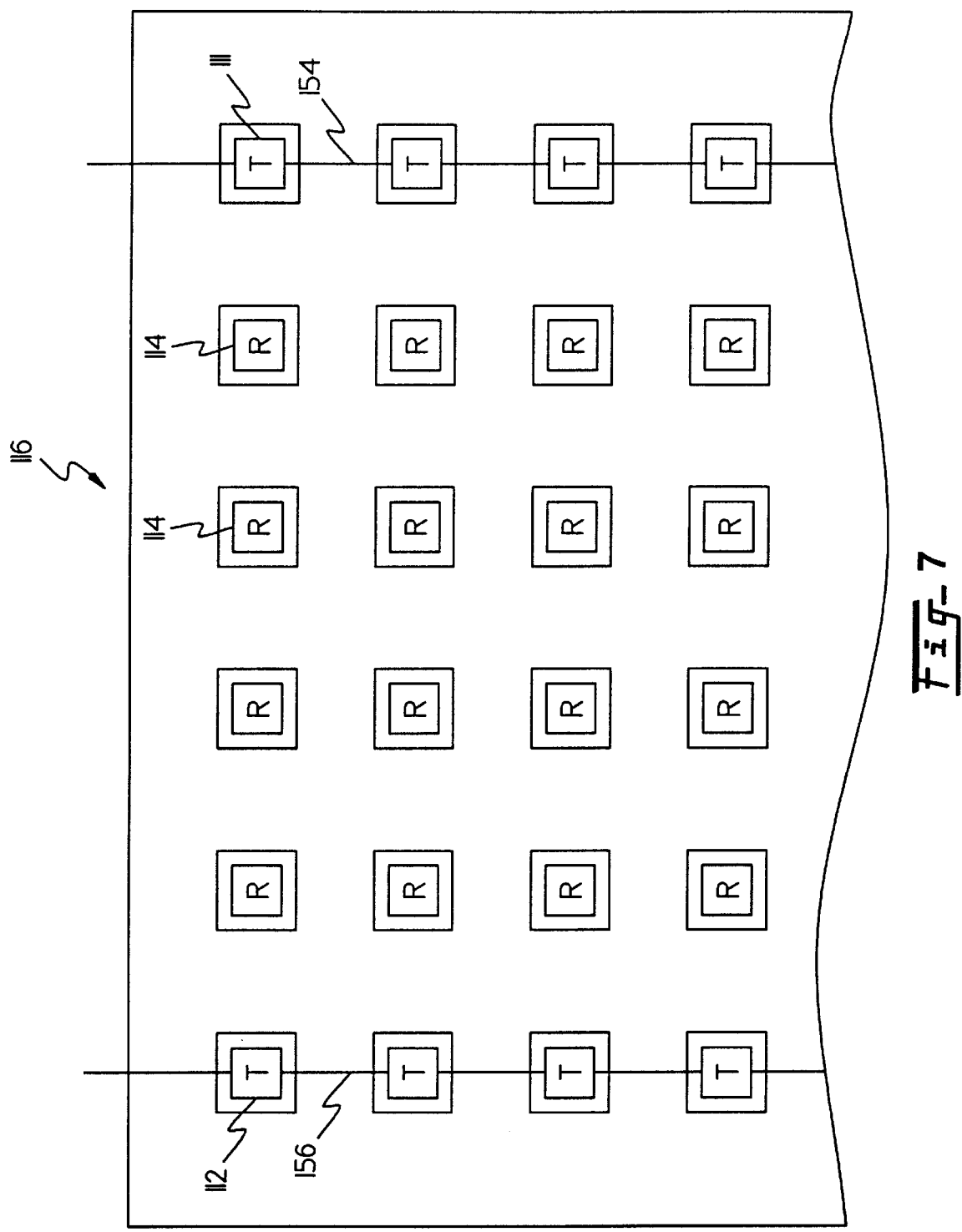

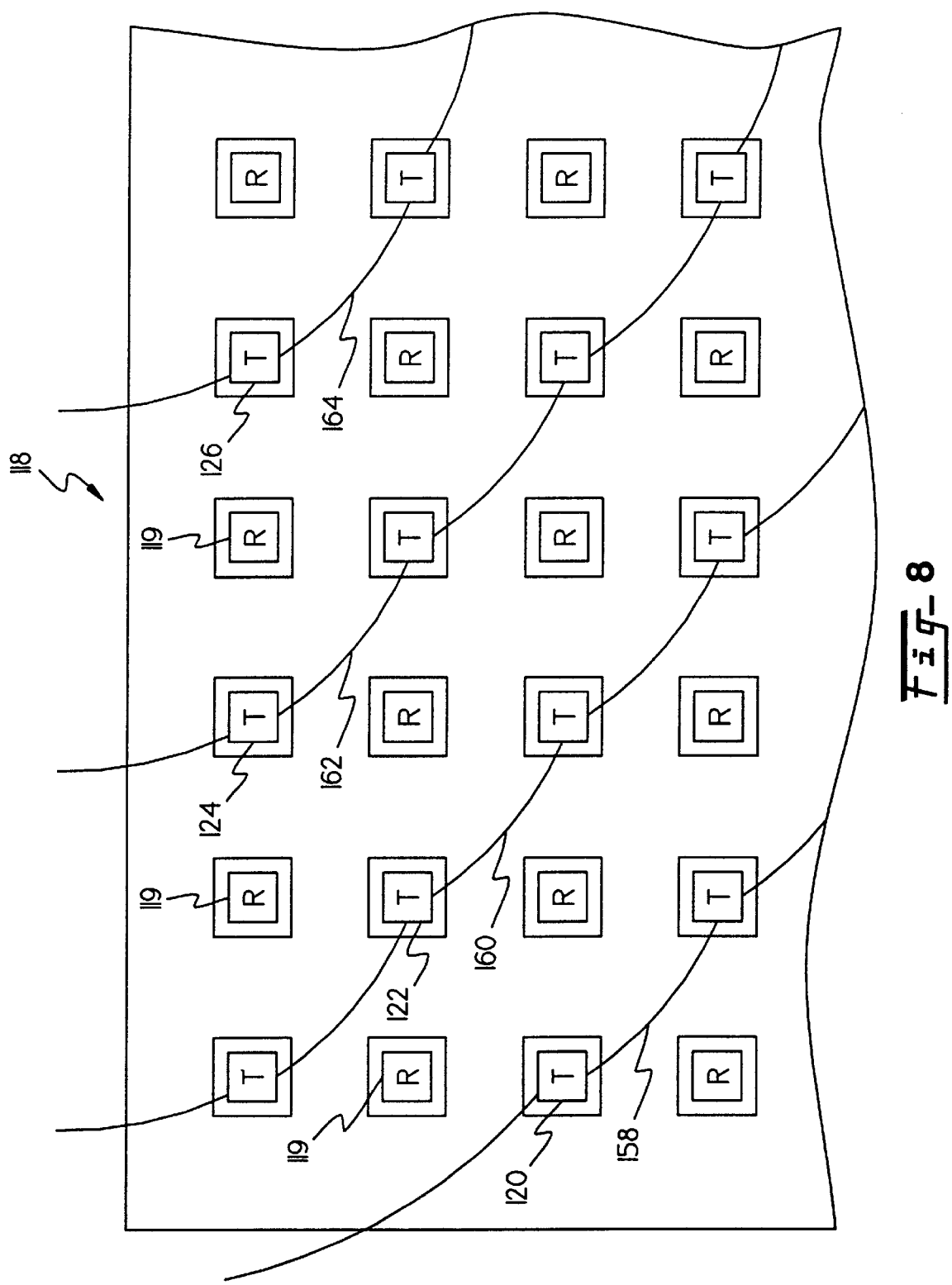

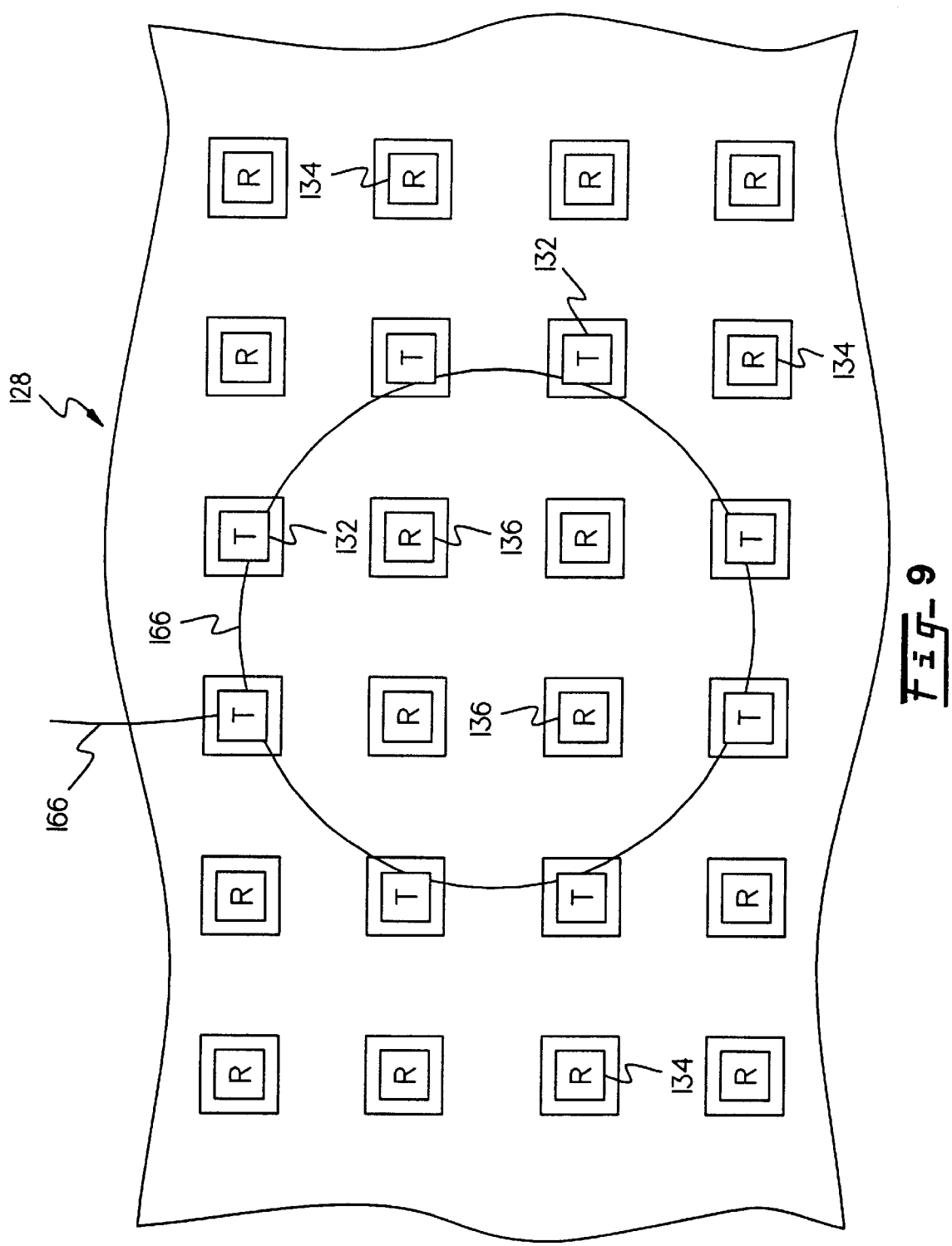

Fig_ 15

DIV: ULTRASONIC CAMERA

CROSS-REFERENCE TO CO-PENDING APPLICATION

This application is a divisional application of copending U.S. application Ser. No. 09/050,224, filed Mar. 28, 1998, which is a continuation-in-part of U.S. application Ser. No. 08/621,112, filed Mar. 22, 1996, now U.S. Pat. No. 5,732, 706 issued Mar. 31, 1998.

FIELD OF THE INVENTION

The invention relates to an ultrasound camera imaging system and, more particularly, to an ultrasound imaging array with a high efficiency and aberration corrected ultrasonic lens, a quasi incoherent transmitter, a low volume fraction transducer based array and a stretched membrane interface.

BACKGROUND OF THE INVENTION

Practical applications of ultrasonic imagers have suffered from pool ultrasonic lenses. These lenses have poor ultrasound transfer characteristics that attenuate the ultrasonic signal and introduce ultrasonic aberrations. Additionally, ultrasonic imagers have used a coherent ultrasound source for insonification of the object. A coherent ultrasound source does not provide a high quality ultrasound image. The resulting image is "speckled", in a manner somewhat similar to an image obtained by a laser. Additionally, an ultrasonic imager requires a method of effectively coupling an ultrasonic lens to an ultrasonic sensor with low signal loss.

Ultrasonic sensors are used in a wide range of applications, particularly medical imaging. Acoustic arrays configured as a two dimensional array of sensors using integrated circuit technology have been developed. Once such acoustic array, is disclosed in U.S. Pat. No. 5,483,963 to Butler et al., issued Jan. 16, 1996, wherein certain rights have been assigned to the assignee of the instant application. U.S. Pat. No. 5 483,963 is incorporated herein by reference. Butler et al. disclose a plurality of ultrasonic transducers arranged in a reticulated two dimensional array, each sensor having a first independent electrical connection, and each sensor having a second common electrical connection. An integrated circuit signal processing means for processing signals from the two dimensional array of ultrasonic transducers is connected to each one of the plurality of ultrasonic transducers at the first independent electrical connection.

While known ultrasonic systems are useful, their operation is sometimes impeded by cross talk interference transmitted from one ultrasonic transducer to another. Therefore, it is a motivation of the present invention to provide an improved ultrasonic image using a sensor that reduces such deleterious effects from cross talk.

Further, transmitter elements in an ultrasonic system require relatively high voltage. Therefore, known ultrasonic arrays comprise circuitry capable of operating under high voltage conditions. The use of such relatively high voltage precludes constructing electronic integrated circuits to operate both receiver and transmitter elements with low voltage CMOS integrated circuit technology. CMOS has inherent advantages of relatively small size and low power. Therefore, it is another motivation of the present invention to provide an ultrasonic system comprising a low voltage receiver array electronics having high voltage transmitter circuitry in the same integrated circuits.

Ultrasonic systems use an ultrasonic transducer to convert electrical energy into sound energy. The sound energy produced is directed at an object, such as biological tissue, or objects immersed in water. Objects in the ultrasonic wave path reflect ultrasonic signals back to the ultrasonic transducer with varying degrees of efficiency. The transducer detects sound that is reflected back to the transducer and provides signals that may be processed to produce an image of the object.

Ultrasonic transducers are provided in linear transducers or rectangular transducers, wraith an array of ultrasonic detectors and transmitters. A lens system is incorporated in the system to focus the ultrasonic signal on the detector.

The performance of ultrasonic transducer systems may be improved by increasing the amount of ultrasonic energy available to the ultrasonic detector. This may be accomplished with a more efficient lens system.

Ultrasonic lens systems suffer from aberrations caused by astigmatism, coma, spherical aberration and distortion. These aberrations reduce the ability of the ultrasonic imager to resolve fine detail and may render the imager unsuitable for a given application.

Accordingly, there is a need for an ultrasonic imager having a high efficiency lens incorporating an efficient sensor/lens interface with a quasi incoherent transmitter utilizing a low volume fraction transducer.

SUMMARY OF THE INVENTION

The invention provides an ultrasonic camera comprising a camera housing and a means for collecting ultrasonic energy at high efficiency with high accuracy connected to the camera housing. The camera further has a means for transducing the collected energy into electrical signals, and a means for processing the electrical signals into an image.

The invention further provides an apparatus for generating, quasi incoherent ultrasonic insonification with a first group of coherent transmitters. The apparatus for generating quasi incoherent ultrasonic insonification also includes a second group of coherent transmitters where the first group transmits a different ultrasonic signal from the second group.

The invention further provides an acoustic interface having a mount with a flat surface surrounding an opening through the mount. A membrane is stretched over the flat surface. A means for retaining the membrane is attached to the mount and the membrane is held taut to the mount by the retaining means.

The invention further provides an ultrasonic lens system comprising a lens housing having a mount and a plurality of ultrasonic elements attached to the mount wherein the plurality of ultrasonic elements cooperate to transmit ultrasonic radiation at high efficiency with low aberration.

The invention further provides an ultrasonic lens system having a first ultrasonic lens made from polystyrene having a first radius of curvature of about −79.35737 mm, and a second radius of curvature of about −162.88524 mm, with an aspherical surface defined by the equation:

$$Z = \frac{cx^2}{\left(1 + \sqrt{(1 - (1+k)c^2x^2)}\right)} + Ax^4 + Bx^6 + Cx^8 + Dx^{10} \quad (1)$$

where c=1/radius, radius=54.76050 mm, K is the conic constant which is zero 0.0 in this case, A=−0.433031E-05, B=0.594032E-9, C=0.157306E-12, and D=−125397E-15, and a first thickness through the ultrasonic center of 3.72 mm; and a second fluid filled ultrasonic lens made from polystyrene having a third radius of curvature of about 54.76050 mm within a second aspherical surface defined by the equation:

$$Z = \frac{cx^2}{\left(1 + \sqrt{(1-(1+k)c^2x^2)}\right)} + Ax^4 + Bx^6 + Cx^8 + Dx^{10}$$

where c=1/radius, radius=89.89027 mm, K is the conic constant which is zero 0.0 in this case, A=−0.679678E-06, B=0.463364E-11, C=0.146454E-13, and D=−0.179238E-17, a third aspherical surface with a fourth radius of curvature of 89.89027 mm having a fourth aspherical surface defined by the equation:

$$Z = \frac{cx^2}{\left(1 + \sqrt{(1-(1+k)c^2x^2)}\right)} + Ax^4 + Bx^6 + Cx^8 + Dx^{10}$$

where c=1/radius, radius=89.89027 mm, K is the conic constant which is zero 0.0 in this case, A=−0.679678E-06, B=0.473364E-11, C=0.146454E-13, and D=0.179238E-17, and a second thickness through the ultrasonic center of 7.44 mm, a fifth radius of curvature of about −578.81495 mm located about 89.028 mm from the fourth radius, and a sixth radius of curvature of about −578.81495 mm with a third thickness through the ultrasonic center of 2.48 mm.

Other objects, features and advantages of the present invention will become apparent to those skilled in the art through the description of the preferred embodiment, claims and drawings herein wherein like numerals refer to like elements.

BRIEF DESCRIPTION OF THE DRAWINGS

To illustrate this invention, a preferred embodiment will be described herein with reference to the accompanying drawings.

FIG. 4, FIG. 5 and FIG. 6 schematically illustrate patterns of further examples of transducer arrays comprising transmit and receive elements made in accordance with alternate embodiments of the present invention.

FIG. 7, FIG. 8 and FIG. 9 schematically show example patterns of transducer arrays comprising transmit and receive elements using a high voltage circuit path to connect selected transmitter elements.

DETAILED DESCRIPTION OF THE PREFERRED EMBODIMENT

Figure 1:
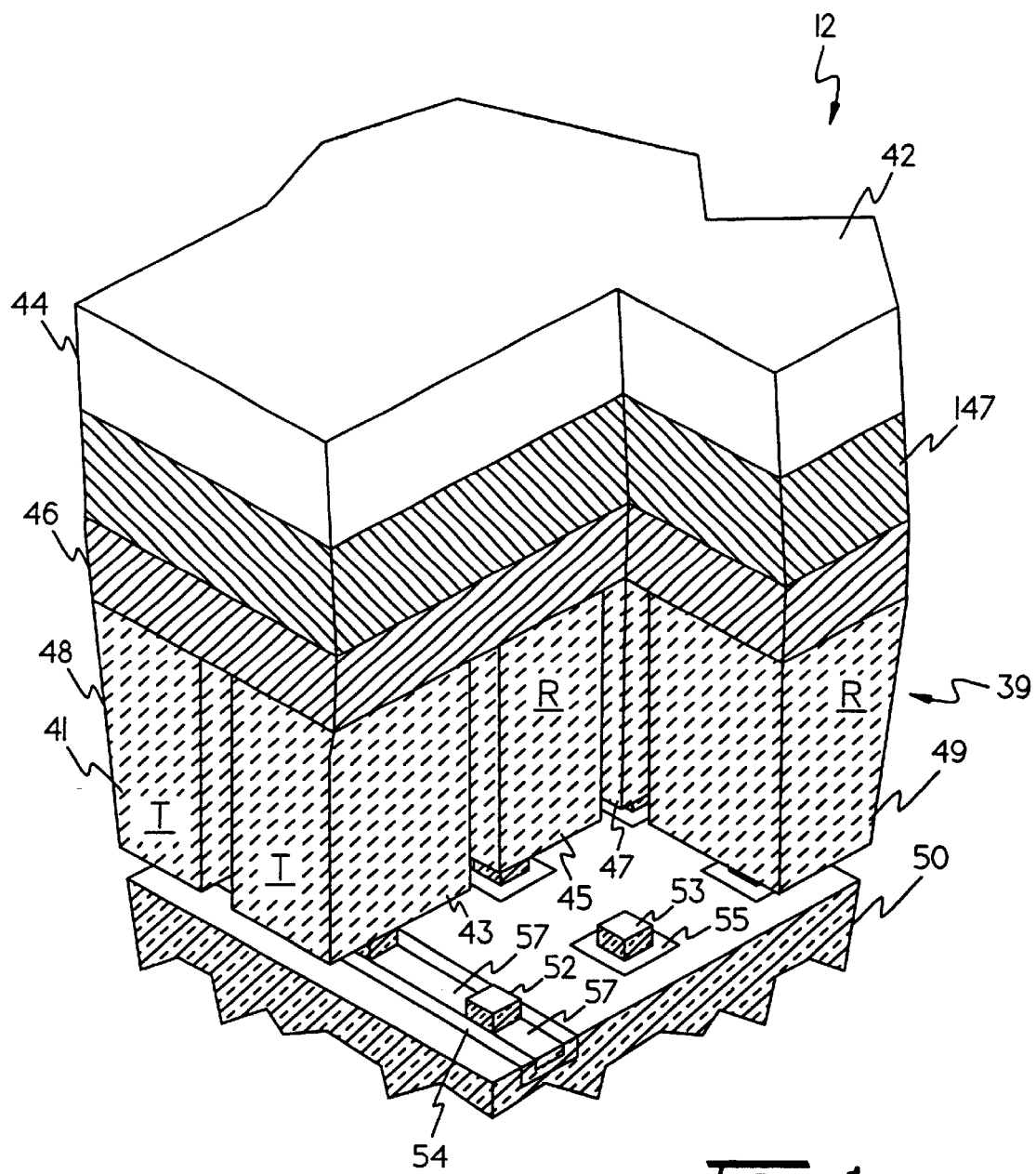
FIG. 1 shows an isometric drawing of a portion of an ultrasonic array and an integrated circuit made in accordance with one aspect of the present invention.

Refer now to FIG. 1, FIG. 1 shows a schematic isometric drawing of a portion of an ultrasonic array and an integrated circuit made in accordance with one aspect of the present invention. The ultrasonic array comprises a plurality of piezoelectric transducer elements, or "piezels", 41, 43, 45, 47 and 49. The piezoelectric transducer elements include interspersed transmitter elements T (such as elements 41 and 43) and receiver elements R (such as elements 45, 47 and 49). Each transducer element, or piezel, 41, 43, 45, 47 and 49 comprises ultrasonic transduction material, such as a suitable composite piezoelectric material known in the art. Indium bumps 52 and 53 bond each receiver element R to an integrated circuit, such as CMOS VLSI integrated circuit 55. Insulation material 54 insulates each transmitter element T from the CMOS VLSI integrated circuit 55. Selected rows or groupings of transmitter elements may advantageously be connected by, for example, high voltage conductor paths 57 wherein the high voltage conductor paths 57 are laid over the insulation material 54 insulating the high voltage conductor paths 57 from semiconductor substrate 50. In the case of a traditional CMOS VLSI circuit, the insulation material 54 may be the same as the circuit passivation layer. Alternatively an insulated metal line within the circuit may, or may not, in turn, be covered with an insulator. It will be understood that a plurality of such high voltage conductor paths 57 may be similarly constructed for connecting transmitter elements throughout an array of elements. High voltage conductor path 57 may advantageously be connected to other similar high voltage conductor paths and to external transmission circuitry (not shown) of conventional design. As a matter of design choice, the high voltage conductor paths may be joined together or separately connected to the external transmission circuitry to enable phasing of transmit elements.

Acoustic array 12 optionally comprises a protective seal and cover with an outer matching layer 44, one or more matching layers 147 and a common electrically conductive electrode 46. By matching the acoustic impedance of the piezoelectric detector 48 with that of body tissue through the use of matching layers 44 and 147, transducer sensitivity increases sharply. The outer matching layer 44 may comprise an acoustic material or composite material having an acoustic impedance suitable for coupling of energy to the transducer elements. Plastic or tungsten-loaded araldite has been used to make quarter wave matching layers. See *Diagnostic Ultrasonics: Principles and Use of Instruments* by W. M. McDicken (1999). The common electrode 46 may comprise a thinner layer of a conductor, such as gold or nickel, for example, for contact to the piezoelectric layer 48.

The individual receiver piezels 45, 47 and 49 may be advantageously hybridized onto the silicon read out IC (ROIC) 55. A saw cut reticulation has been made completely through the ceramic PZT layer 48 up to the common electrode 46. By cutting all the way through the PZT layer 48, electrical and mechanical cross talk can be reduced, thereby improving the resolution of the directed beam, as sell as the sensitivity to the received signal. Cutting of the transducer material 48 through to the common electrode 46 increases inter-element isolation. Furthermore, by using air in between the piezels 41, 43, 45, 47 and 49 as an acoustical insulator, acoustic cross talk can be reduced significantly as well. Air isolation between elements, or a filler material such as epoxy, silicone, plastic or other equivalent materials embedded between elements can significantly reduce cross talk in both directions thus improving system resolution.

It is well known that sub-reticulation within an element may be also used to create a composite detector. The special structure of the device of the invention is particularly well suited for fabrication of two dimensional arrays because the tops of the transducers are connected by the common electrode 46 and matching layers and the other side is connected via the bump bond to the multiplexer.

Figure 21:
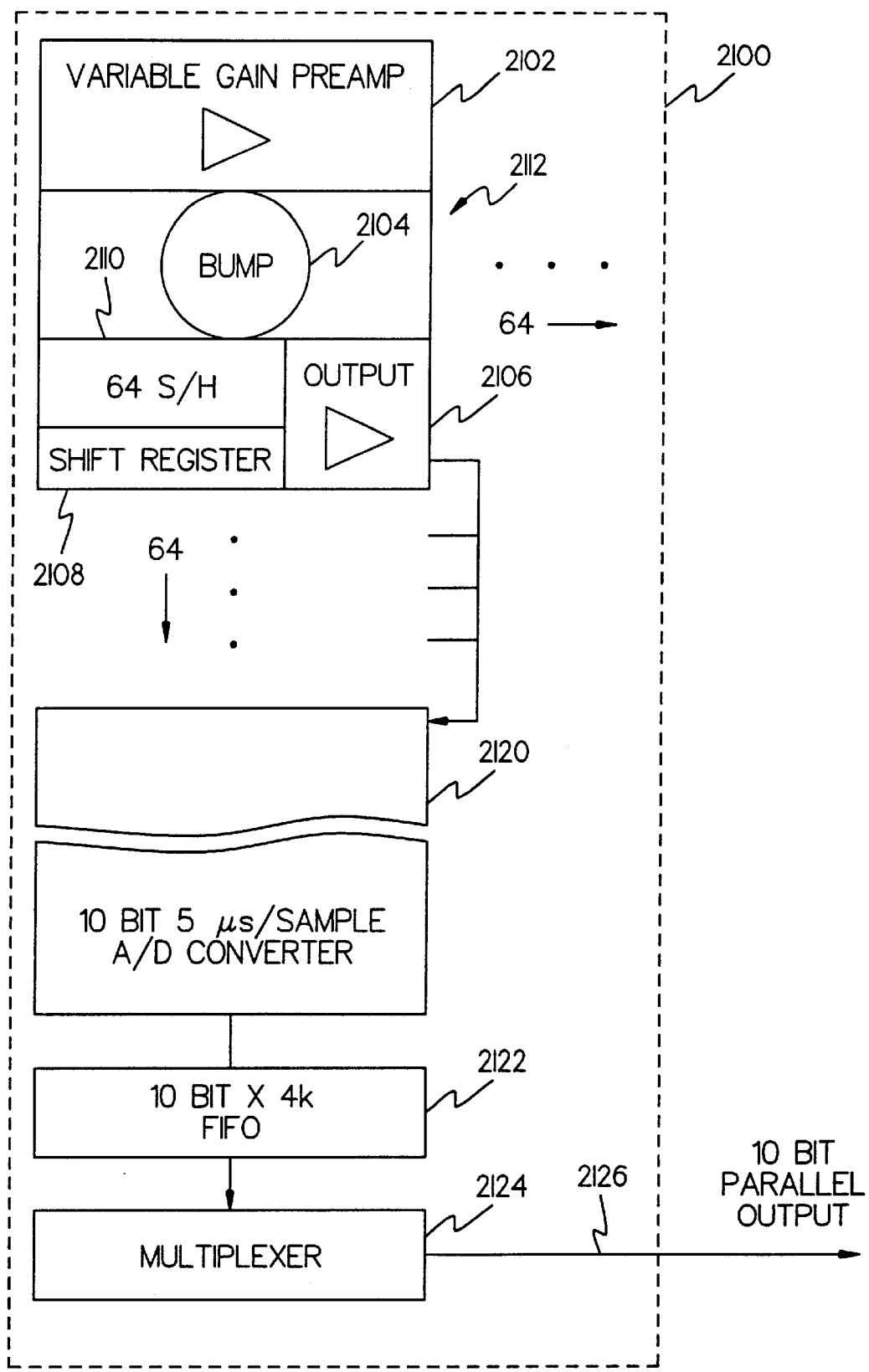
FIG. 21 schematically illustrates one embodiment of on-chip electronic circuitry incorporating an analog-to-digital converter constructed on an integrated circuit employed in one aspect of the invention.

Additional available space on the active surface of the semiconductor allows the integration of other active electronic circuitry, such as pre-amps, sample holds, peak detectors and an on-chip analog-to-digital converter. The integrated analog-to-digital converter as illustrated in FIG. 21 would have the following advantages: reduced power, improved transmission of signals over the cables, and reduced conversion rates by performing analog to digital conversion before multiplexing rather than after signal multiplexing.

Figures 2A, 2B:
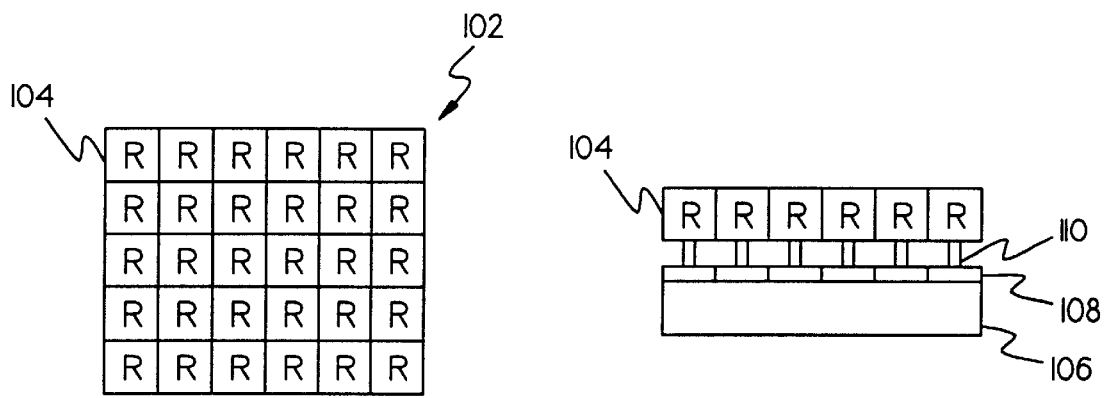
FIG. 2A and FIG. 2B schematically illustrate a top view and a side view, respectively, of a pattern of a receiver array.

FIG. 2A and FIG. 2B schematically illustrate a top view and a side view, respectively, of a pattern of a receiver array, wherein each of the transducers in the array function to receive signals. In one example of such a configuration, a separate array of transmitters (not shown) may be employed to transmit signals. In another example of such a configuration, receiver and transmitter functions may be switched using the same elements, but applying different control signals, as discussed hereinbelow with reference to FIG. 15. In the aforementioned switched configuration, relatively higher voltage DMOS circuitry, instead of CMOS circuitry, may be employed to carry out the functions of ROIC 55. Ultrasound imagery, as traditionally constructed, requires transmission of a single pulse and then "listening" to returning echoes. An image is then constructed from the varying time-dependent intensity of the returned signal. The array permits the sampling and storage for each element directly behind each element. The amount of signal processing and sample storage in the ROIC is limited only by conventional circuit design rules.

Figures 3A, 3B:
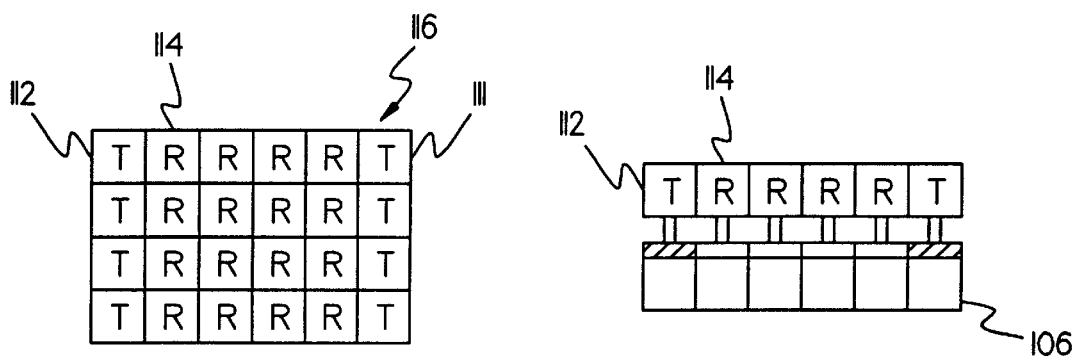
FIG. 3A and FIG. 3B schematically illustrate a top view and a side view, respectively, of a pattern of a transducer array comprising transmit and receive elements made in accordance with one aspect of the present invention.

FIG. 3A and FIG. 3B schematically show an array 116 of receivers 114 and two linear arrays of transmitters 112. FIG. 3A shows a top view of the arrays 116 and FIG. 3B shows a side view of the array 116. FIG. 7 shows power routing for the transmitter arrays of FIGS. 3A and 3B. High voltage and control line 16 is connected to each transmitter 112 in the linear array 116. Similarly, high voltage and control line 154 connects each transmitter in linear array 111. Independent high voltage and control lines 154 and 156 provide independent switching of linear arrays. The multiple transmit elements may advantageously be wired to be pulsed simultaneously or pulsed in groups permitting transmit beam-forming as in conventional ultrasound. Use of the high voltage and control lines 154, 156 enables the transmission of relatively high voltage signals to the transmission elements from an external transmission circuit, wherein the external transmission circuit may be of a conventional design. Thus, since the transmission circuitry may be implemented externally, the ROIC comprises relatively lower voltage CMOS, allowing for very dense circuitry. Thus, the apparatus of the invention allows increased signal processing and/or time sampling to take place in the ROIC. As a result, significant parallel signal processing may be implemented using CMOS circuitry in accordance with known practices.

FIG. 4 schematically shows an array 118 of receivers 119 and four linear arrays of transmitters 120, 122, 124 and 126. Transmitters 120, 122, 124 and 126 are positioned in a diagonal configuration. FIG. 8 shows power routing for the transmitter arrays of FIG. 4. High power line 158 is connected to each transmitter in linear array 120. Similarly, high power line 160 connects each transmitter in linear array 122. High power line 162 connects each transmitter in linear array 124 and high power line 164 connects each transmitter in linear array 126. As in the configuration of FIG. 7, independent high power lines provide independent switching of linear arrays 154 and 156.

FIG. 5 schematically shows an array 128 of receivers 134 and transmitters 132. The transmitters 132 are configured in generally circular arrangements 130, 132. FIG. 9 shows a generally circular arrangement of transmitters 132 among receivers 134. High voltage and control line 166 is connected to each transmitter, in generally circular arrangement of transmitters 132. Outer circular arrangements of transmitters are provided with separate switching lines to provide independent activation of each set of transmitters.

FIG. 6 schematically shows an array 138 of receivers 148 and a predetermined pattern of transmitters 140, 142, 144 and 146. Independent high voltage and control lines may be connected to each transmitter independently or each transmitter may be connected by a single high power supply line.

As discussed above with respect to, for example, FIG. 3A, in one embodiment of the invention, the arrays are built with low voltage CMOS. Use of CMOS, as compared to other circuit technologies, allows miniaturization that permits dynamic electronic focus in both directions using cell based logic and circuitry. A form of such dynamic electronic focusing is known in the field of phased array radar, but was previously limited in ultrasound to steering the beam in one direction only; such as in transmit only, receive only, or both. The two dimensional array with active circuitry directly behind each element makes possible focusing or steering the beam in both directions. The result of such focusing and steering is a sharper picture and/or increased flexibility.

Figure 10:
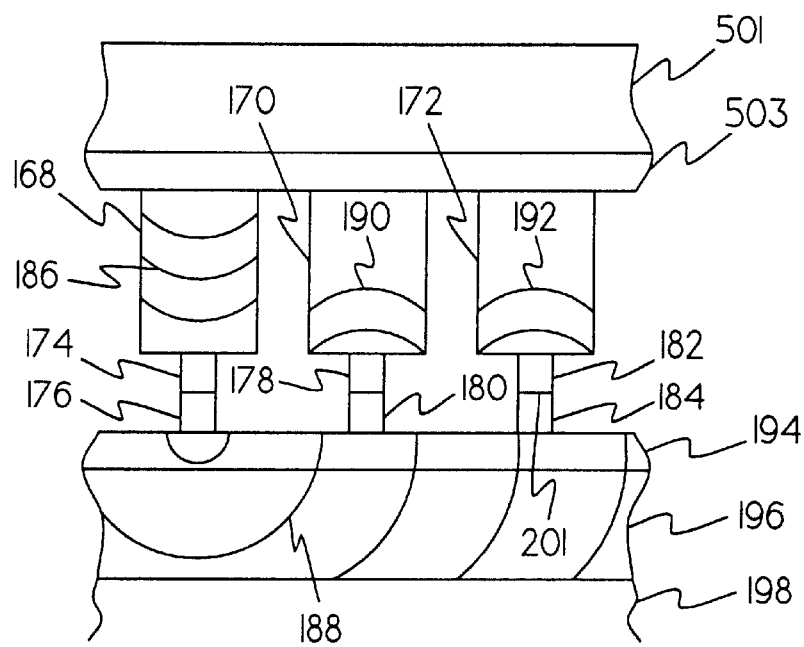
FIG. 10 illustrates cross talk properties in an ultrasonic array.

FIG. 10 illustrates the effect of signal cross talk. Signal cross talk is generated by the operation of one piezel affecting other elements of the array. Element 168, connected by indium bump bond 174 to bump bond 176 connects to active device layer 194. Active layer 194 is deposited on semiconductor substrate 196. Ultrasonic element 168 receives or transmits signal 186. Signal 186 is shown as a wave train that propagates to the other array elements such as transducer elements 170 and 172. Active layer 194 and substrate 196 act to transmit waves or portions of waves 188 of the signal 186 though indium bump bonds 180 and 178 to element 170. Cross talk generates wave train 190 in piezel 170. Active layer 196 and substrate 194 act to transmit waves 188 of signal 186 though indium bump bonds 184 and 182 to element 172. Cross talk generates wave train 192 in piezel 172.

The size of the bump interconnections 182 and 184, 178 and 180, 174 and 176 is particularly significant in controlling the acoustic properties of the back surface of the transducer 168, 170 and 172 and thus also the cross talk resulting from acoustic energy received or transmitted by one element that subsequently influences another neighboring element. Ideally, transducer elements would be completely isolated. If such were the case, then energy impinging on, or transmitted by, one element would have no effect on its neighbors and each element would be independent. Air is an excellent isolator for ultrasound but, without the structure of the present invention, there has not been a means to approach the ideal case. Prior to the present invention, problems associated with reducing cross talk were in the physical implementation of the transducer array structure. In order to sense the electrical energy in the transducer. there must be either a hard electrical connection or an extremely efficient and precisely impedance-matched capacitive coupling established. Historically, structures employed have been constrained for fabrication purposes to being held together with appropriate attenuating or reflecting adhesives and glues to absorbing conductive substrates. In contrast to previously known structures, the new structure of the present invention approximates the ideal case. The top surface is connected only by the common electrode 503 which is incorporated into the matching layer 501. The bottom of the transducer 192 is contacted only by bump 182. The sides are isolated by air or other material as discussed above to improve mechanical stability. If the bump 182 is maintained at a size which is small with respect to the element end area, cross talk transmitted by the bump becomes insignificant and can be ignored. Maintaining a bump size less than about 10–20% of the size of the piezel contact area appears from electrical models to be the critical point where the size effect is most significant. This is a direct function of bump area with respect to element area.

The primary effects from any mechanical connection which are undesirable are: (a) conduction of the ultrasound energy into the mounting surface where it would be re-radiated and detected by neighboring elements; and (b) constraint of the transducer material by the contact which would prevent the full piezoelectric response. Of these two effects, the first is the larger and more deleterious, but both are reduced by small contacts. If the bump required the full area, then the amount of energy transferred into the substrate would only be a function of the acoustic properties of the bump material with respect to the transducer material and the substrate. For the simplified case of no attenuation by the bump, all energy falling on each element should be re-radiate to its neighbors with only the attenuating properties of the substrate to control re-radiation. However, if the bump is small, it will act as an attenuator because only the area fraction occupied by the bump will conduct the energy. Thus, with a 10% area fraction, only 10% of the energy will be conducted into the substrate. To be sensed by a neighbor, the energy must pass through a second 10% attenuator and thus reduced by another factor of ten. The result would be 1% cross talk, 99% attenuation, if the bump and substrate had no attenuating properties. If the bump area were reduced to 5%, a 0.25% cross talk, 99.75% attenuation, would result.

This effect is independent of the substrate, and so would be equally applicable for traditional transducers and substrates including, but not limited to, read out integrated circuits. This effect permits electrical contact to the isolated side of a transducer without adding a significantly acoustically conductive path.

Figure 11:
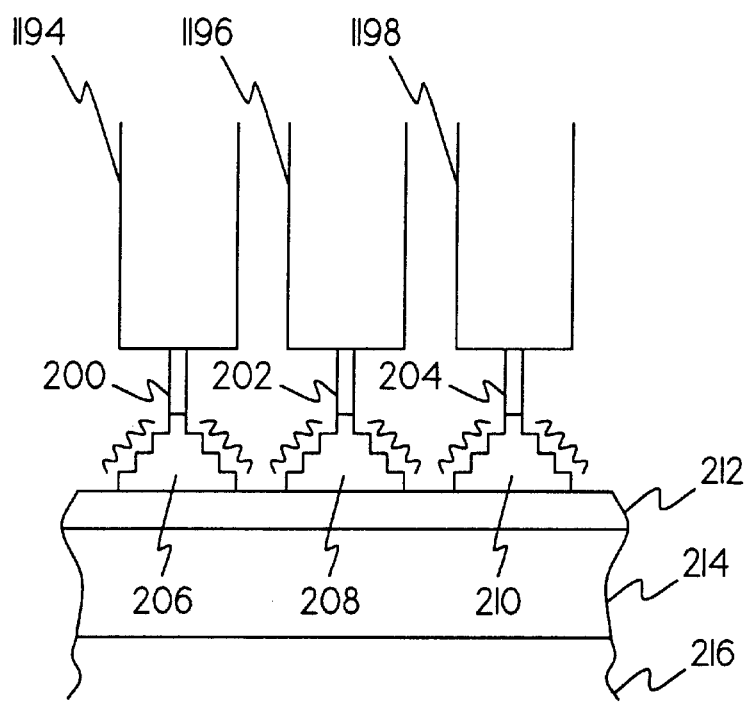
FIG. 11 schematically illustrates a cut away side view of an alternate embodiment of the bump bonding features of the invention.

FIG. 11 shows one alternate aspect of the invention to reduce signal cross talk. Small indium bumps 200, 202 and 204 connect transducer elements 1194, 1196 and 1198 to stepped bond connectors 206, 208 and 210, respectively. Stepped bond connectors 206, 208 and 210 and bumps 200, 202 and 204 are surrounded by an electrically insulating material such as air, one of many known epoxies or silicone based materials. Filler material, if desired, can be injected into the gap around the bump bonds to provide stabilization. Selection of the filler material may be based upon acoustical and electrical impedance to minimize cross talk. The graded structure of the stepped bond connectors permits the tailoring of the acoustic properties of the interconnection layer 212 between the piezoelectric elements and the mounting substrate 214. By adjusting the area and volume fractions of the electrical connections, the acoustic properties of the interconnection layer can be adjusted.

Figure 12:
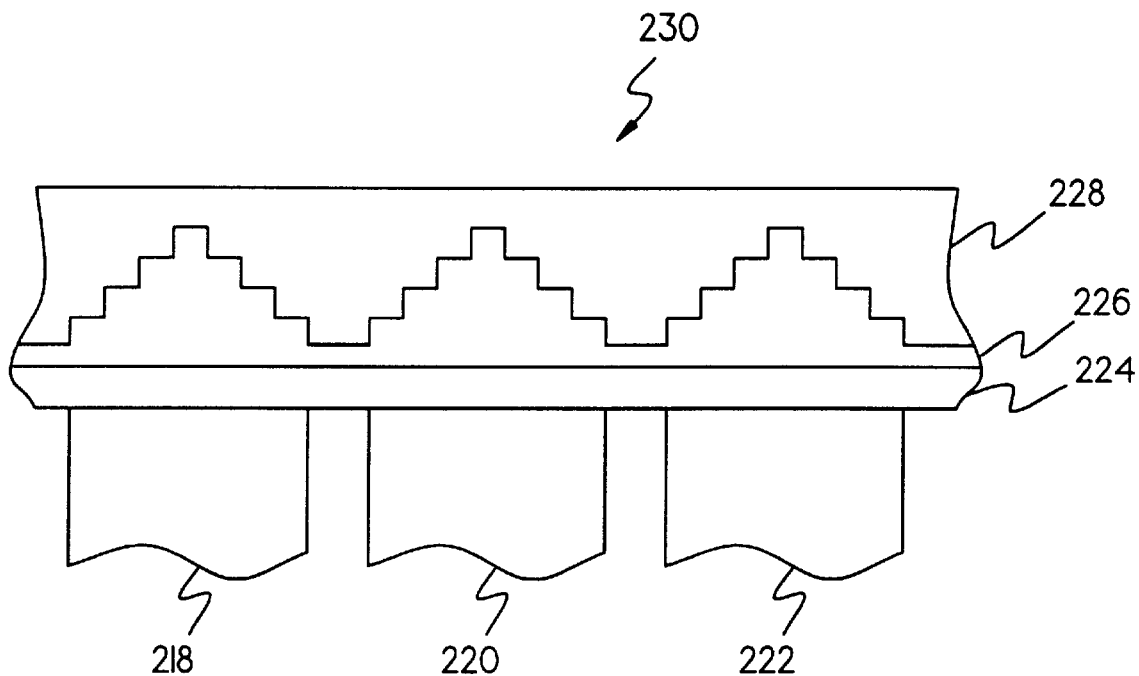
FIG. 12 illustrates a further alternate embodiment of a matching layer.

FIG. 12 shows a cross section of a stepped matching layer for array 230. Common electrode 224 is connected to matching layer 1226, which on one side is flat and on the other is configured in a step arrangement. Matching layer 2228 has a matching step arrangement. Transducers 218, 220 and 222 are connected in the fashion of FIG. 1 to common electrode 224. The stepped matching layers act to dampen cross talk signals generated by transducers 218, 220 and 222. The step sizes in matching layers 226 and 228 are selected to be small with respect to the wavelengths of the ultrasound.

Figure 13:
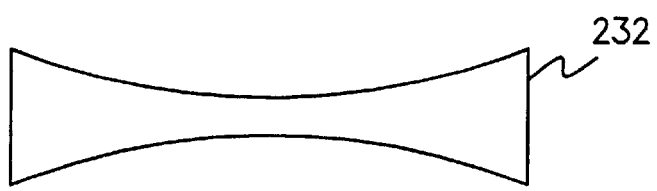
FIG. 13 schematically shows an example of an ultrasonic lens.
Figure 14:
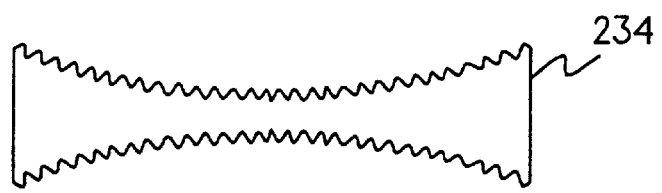
FIG. 14 schematically shows an example of a matching layer created in the surface of the lens.

FIG. 13 shows a concave lens of the invention and FIG. 14 shows a serrated concave lens of the invention. The prior art is constrained to select materials which have the desired acoustic properties as intrinsic properties. As contemplated by the present invention, desired material properties may be constructed from two different materials. Surface finish geometries of lateral area and thickness may advantageously be selected to be significantly less than a wavelength in order to reduce diffraction effects. In the simplest case, if graded material properties were to be constructed, binary optic structures might be used to make a graded interface, where one side of the interface fully comprised a first material, the other side comprised an entirely different material and the intervening layers comprised different area fractions of the two materials. This could be expanded to have multiple materials in the stack to yield multiple variable properties. Or, if there bias no material with the correct initial properties, such a graded or sloped structure could be constructed from two different materials applied in the proper area percentage to obtain a desired average properties.

Some experimental evidence in support of this approach is available. Lenses were fabricated by Lockheed Martin IR Imaging Systems. Inc. of Lexington, Mass. USA. The lenses are relatively rough but, because the roughness is less than wavelength dimensions, there is little or no effect, as evidenced by an excellent, nearly theoretical performance of the lens. In another example of a matching layer, a lens having an inherent surface roughness may be used in the above type of structure in the lens surface. The surface may advantageously be immersed in fluid that fills any open space between the lens and the transducer array, thereby creating an inherently graded matching, anti-reflection surface without a coating. Creating such a graded lens surface may be done using any suitable known process such as, for example, machining, molding, or any method of material deposition. The possibility of molding in ridges is particularly attractive since it would require no additional steps to create a graded matching surface. Furthermore, the approach, because it incorporates the fluid surrounding the lens, is inherently self correcting if the fluid properties change significantly.

Figure 15:
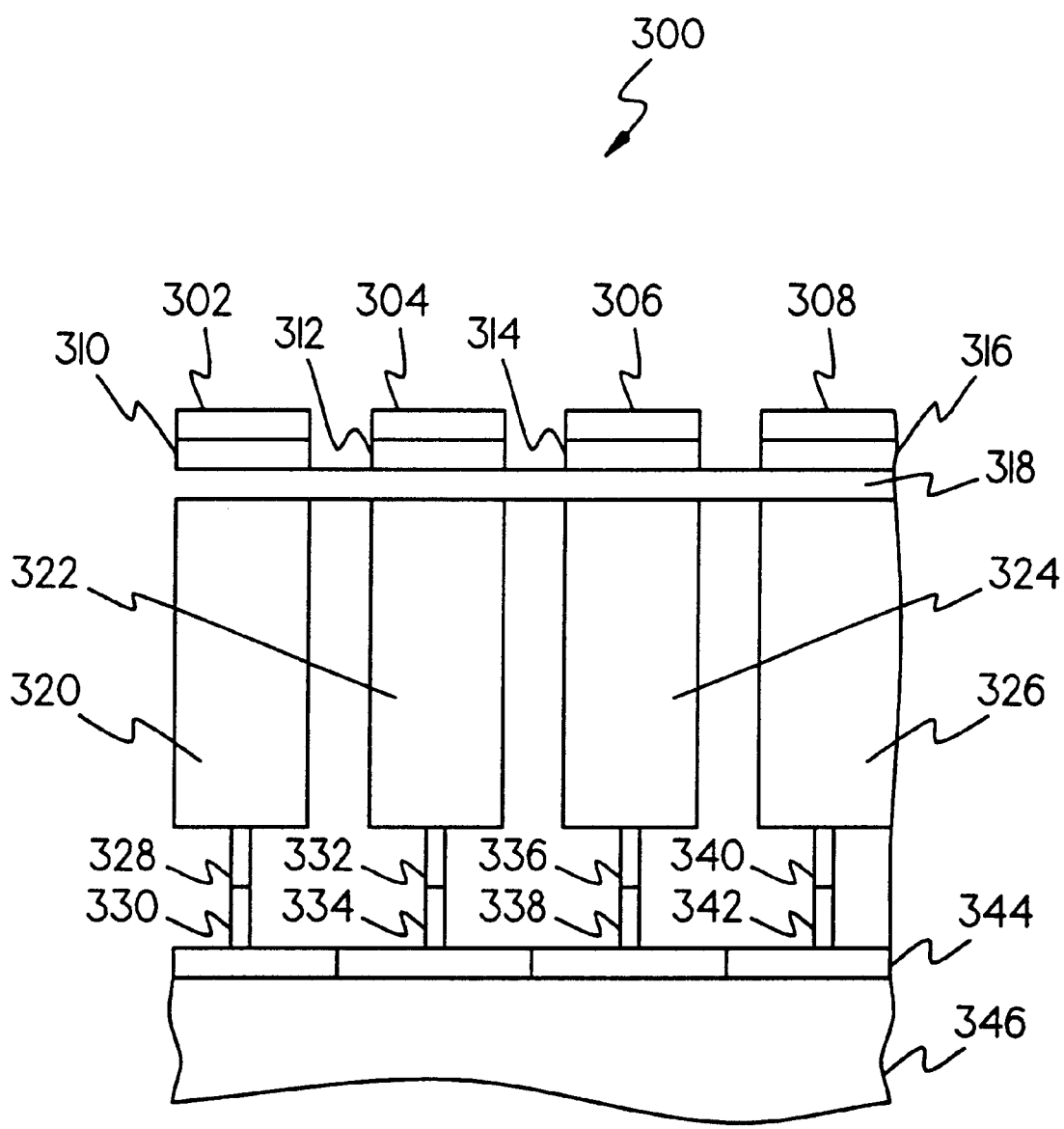
FIG. 15 schematically shows a cut away view of a partial ultrasonic array made in accordance with one aspect of the present invention.

FIG. 15 shows an alternate embodiment of the invention including an any of transducers 300. Cross talk is reduced in the configuration of FIG. 15 by isolating upper and lower matching layers by cutting in between the matching layers for each transducer. Common electrode 318 serves to connect one side of the transducer array. Transducers 320, 322, 324 and 326 may advantageously be indium bump bonded to active layer 344. It is believed that full reticulation of the upper and lower matching layers, up to the common electrode 318, results in better signal coupling and better isolation between elements.

Figure 16:
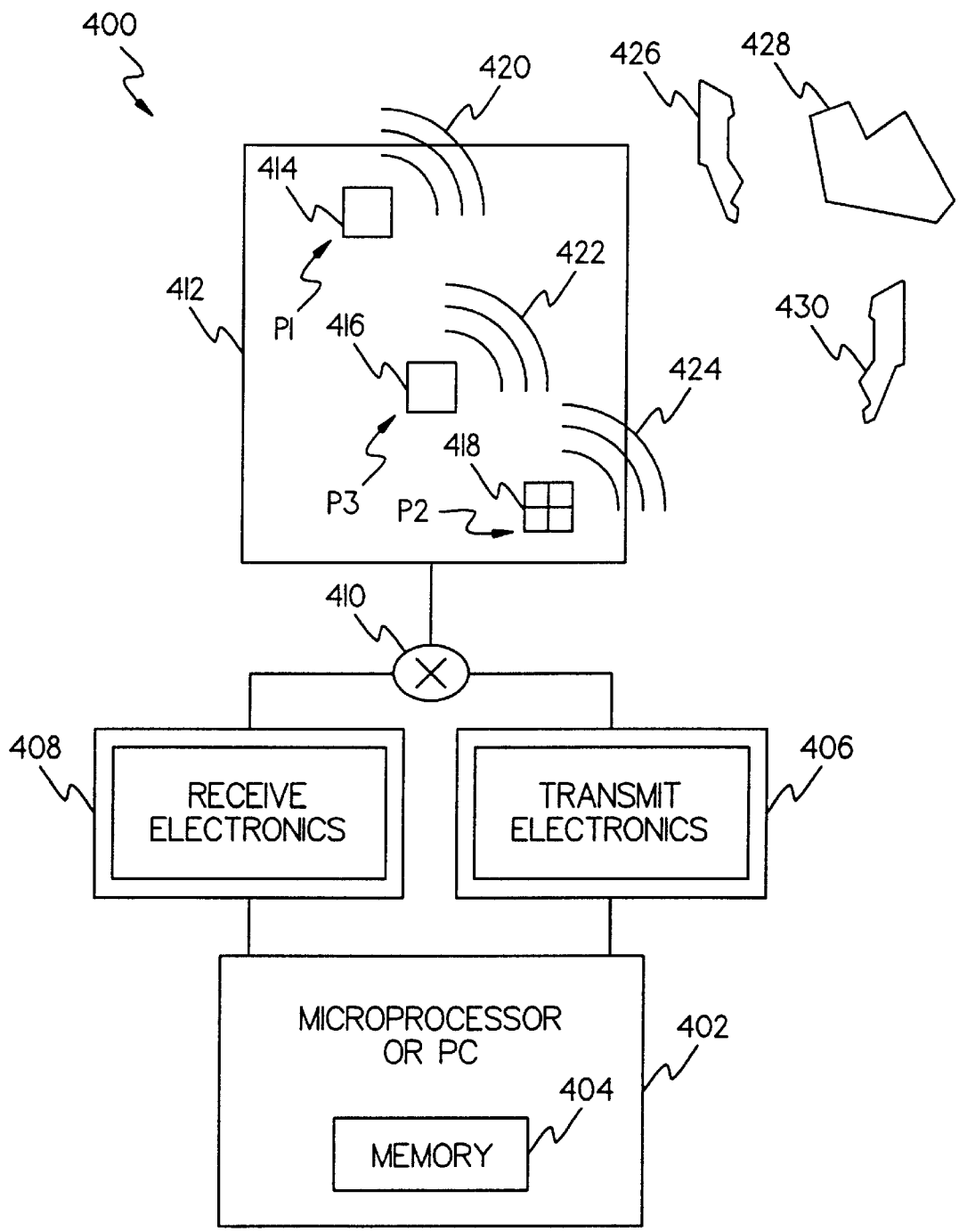
FIG. 16 shows a schematic of an ultrasonic array and system of the invention imaging a target.

FIG. 16 shores a schematic of the array 412 of the invention imaging a target 428. Piezoelectric array 412 comprises a plurality of piezels represented by piezels 414, 416 and 418. Alternately, FIG. 16 could function in a bistatic mode with separate transmit and receive transducers but with similar microprocessor or PC monitoring, control and selection of any suitable combination of transmit elements and receive elements. High voltage switch 410 switches the signal from the array to either the receive electronics 408 or the transmit electronics 406. The receive electronics 408 interface to a microprocessor or personal computer 402 having a memory 404 in a conventional manner. The transmit electronics also interface to the microprocessor or personal computer 402 in a conventional manner. The microprocessor 402 stores the identity of those piezels that provide a usable signal from the target 428. The array may be scanned in a regular fashion or in a random fashion to determine which piezels should be used. In one embodiment of the invention, clusters of piezels may be used to boost signal strength. For example, groups of piezels of predetermined number, such as 4, 9 or 16 piezels, are triggered to send out a pulse. The signal returned from the target is evaluated for clarity. If the signal is useable from a particular piezel the identity of the piezels is stored in memory 404. If the signal returned from the target is unusable, or has a relatively low signal to noise value, the piezel is deleted from this array/target combination because probably both transmit and receive capability is compromised simultaneously.

For example, during an echo cardiogram using a large array that may be an inch or two along one axis, some of the elements would be blocked by rib bones 476. 430. The signal from the blocked piezels would not be used to receive or transmit. In this example, since each element is a transmitter or receiver, the array could be constructed from DMOS. In one alternate embodiment of the invention, some piezels may be phased differently to improve sensing of the target. The computer would select spatial location of the piezels used to sense the target and can additionally temporally adjust the send/receive waves so that they are optimized for best clarity.

In one embodiment, the high voltage switch is comprised of a DMOS, or double diffused metal oxide semiconductor, transistor. In an alternate embodiment, one or more of the high voltage switches may be electrically actuated to connect the complementary ultrasonic transducer to the camera's electrical ground. In another embodiment, the activation of the high voltage switches is controlled by a microcontroller, microprocessor or other semiconductor device. In another embodiment, the pattern of activation of the high voltage switches creates one or more groups of transmitters from the plurality of transmitters. In another embodiment, one or more groups of transmitters selected by the high voltage switches are driven sequentially through the common electrode to produce separate images of the object. In another embodiment, the signal processor connects these sequential images to produce a high quality image. In another embodiment, a DC voltage is applied to the common electrode and a pattern of high voltage switches are connected to an electrical around by a short activation pulse or a series of activation pulses to create an ultrasonic transmitter pulse, in another embodiment, the common electrode is connected to an electrical ground and a pattern of high voltage switches are connected to a DC voltage on the substrate by a short activation pulse or a series of activation pulses to create an ultrasonic transmitter pulse.

Figure 17:
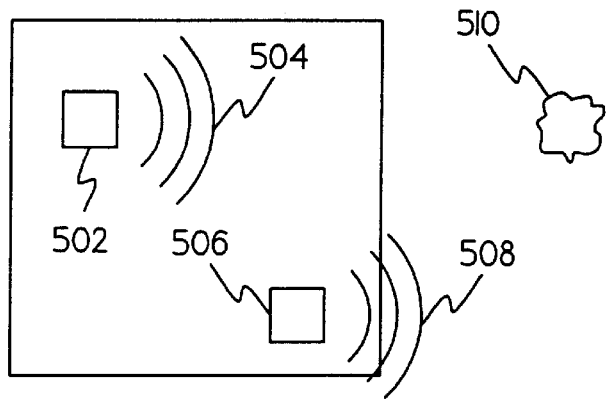
FIG. 17 shows an example of target imaging optimization in accordance with one aspect of the invention.
Figure 18:
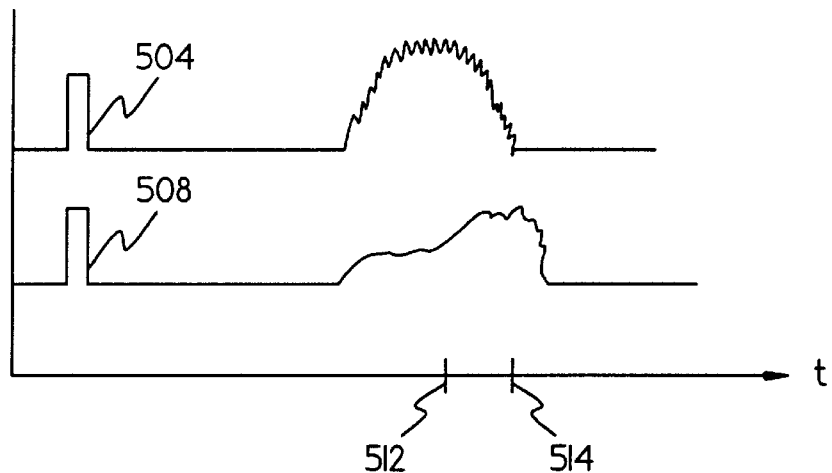
FIG. 18 shows phasing time information of typical piezels illustrated in FIG. 17.

Now referring to FIG. 17 where an example of target imaging optimization is shown. A first piezel 502 transmits a pulse 504. A second piezel 506, spatially separated from the first piezel 502, transmits a pulse 508. As shown in FIG. 18, first piezel 502 may best highlight target tissue 510 at time 512 and second piezel 506 may best highlight target tissue 510 at time 514. The computer 402 stores the preferred phasing time information of each piezel 502, 506 so that a composite picture from each piezel 502, 506 is made from the best temporal data. The computer optimizes an image by selecting piezels spatially, and associating a preferred phasing for each selected piezel.

Figure 19:
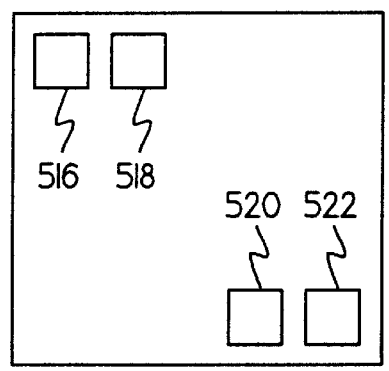
FIG. 19 illustrates transmit piezels having spatially associated receive and/or transmit piezels.

In one embodiment, the first piezel 502 and the second piezel 506 may each comprise a transmit and receive piezel. In an alternative embodiment, as shown in FIG. 19, each transmit piezel 516, 520 may have a spatially associated receive piezel 518, 522. For example, a checkerboard pattern of transmit piezels and receive piezels would provide for spatially associated transmit and receive elements. In both embodiments, the computer 402 stores the preferred phasing time between transmission and reception to provide for optimal phasing.

Figure 20:
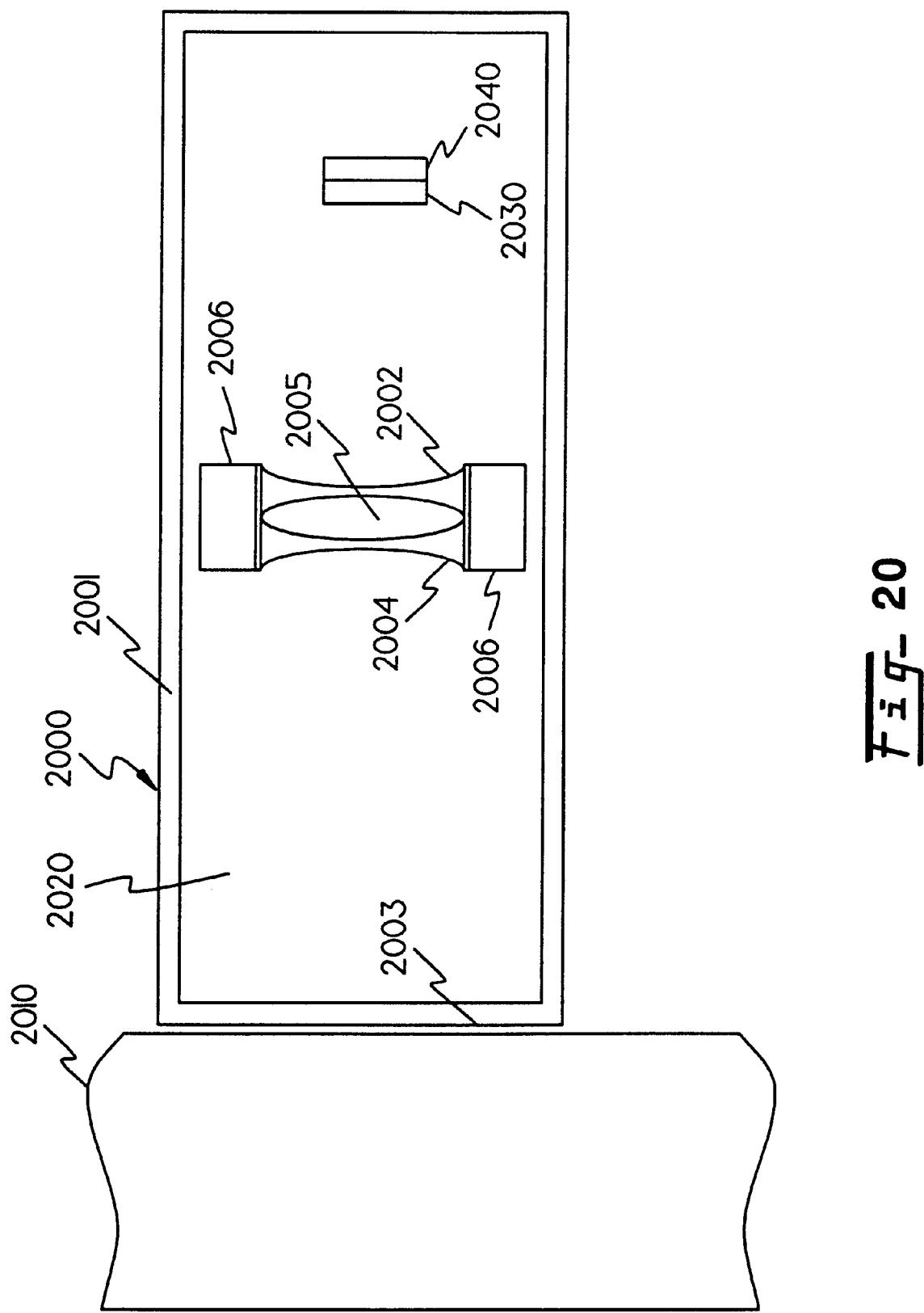
FIG. 20 schematically illustrates an overview of an ultrasonic system of the present invention employing a multi-element acoustic lens.

Now referring to FIG. 20, an overview of an ultrasonic system of the present invention employing a multi-element acoustic lens is schematically illustrated. The ultrasonic system 2000 includes a housing 2001, an ultrasonic window 2003, a multi-element lens 2005, piezoelectric material 2030, silicon integrated circuit 2040 and optional transmit transducers 2006.

In operation, the ultrasonic window 2003 may be in contact with, for example, body tissue 2010. The multi-element acoustic lens may comprise at least two lenses 2002, 2004 where lenses 2002, 2004 may be constructed as discussed hereinabove with reference to FIG. 14, for example. Piezoelectric material 2030 may be constructed as one of the ultrasonic arrays as described herein. Optional transmit transducers 2006 may be of conventional design or be constructed in accordance with an embodiment of the apparatus of the present invention as described hereinabove. The housing 2001 may advantageously be filled with a known ultrasound coupling fluid 2020 or equivalent. Piezoelectric material 2030 and Silicon integrated circuit 2040 are electrically connected as described herein with, for example, bump bonding techniques.

FIG. 21 schematically illustrates one embodiment of an analog-to-digital converter constructed on an integrated circuit 2100 employed in one aspect of the invention. The integrated circuit 2100 comprises a plurality of similarly constructed unit cells 2112, an analog-to-digital converter (ADC) 2120, a buffer 2122 and a multiplexer 2124. In one useful embodiment, 64 such unit cells may be constructed on a silicon die of about 12 mm by 10 mm.

Each unit cell 2112 may comprise a bump 2104 for connection to an ultrasonic transducer array, a sample-and-hold circuit 2110, a shift register 2108, a variable gain preamplifier 2102 and an output 2106. The elements are connected and operate according to conventional integrated circuit design rules. Each unit cell output 2106 is coupled to an on-clip ADC for converting analog, signals representing ultrasonic energy to digital signals for further processing. In one useful embodiment, the on-chip ADC 2120 may comprise a 10 bit, 5 microsecond/sample ADC. The ADC 2120 is coupled to a buffer such as, for example, a first-in-first-out (FIFO) buffer 2122. Buffer 2122 is coupled to a multiplexer 2124 that provides an output 2126 to external processing circuitry. In one example embodiment of the invention, the multiplexer output may be a 10 bit parallel output.

Figure 22:
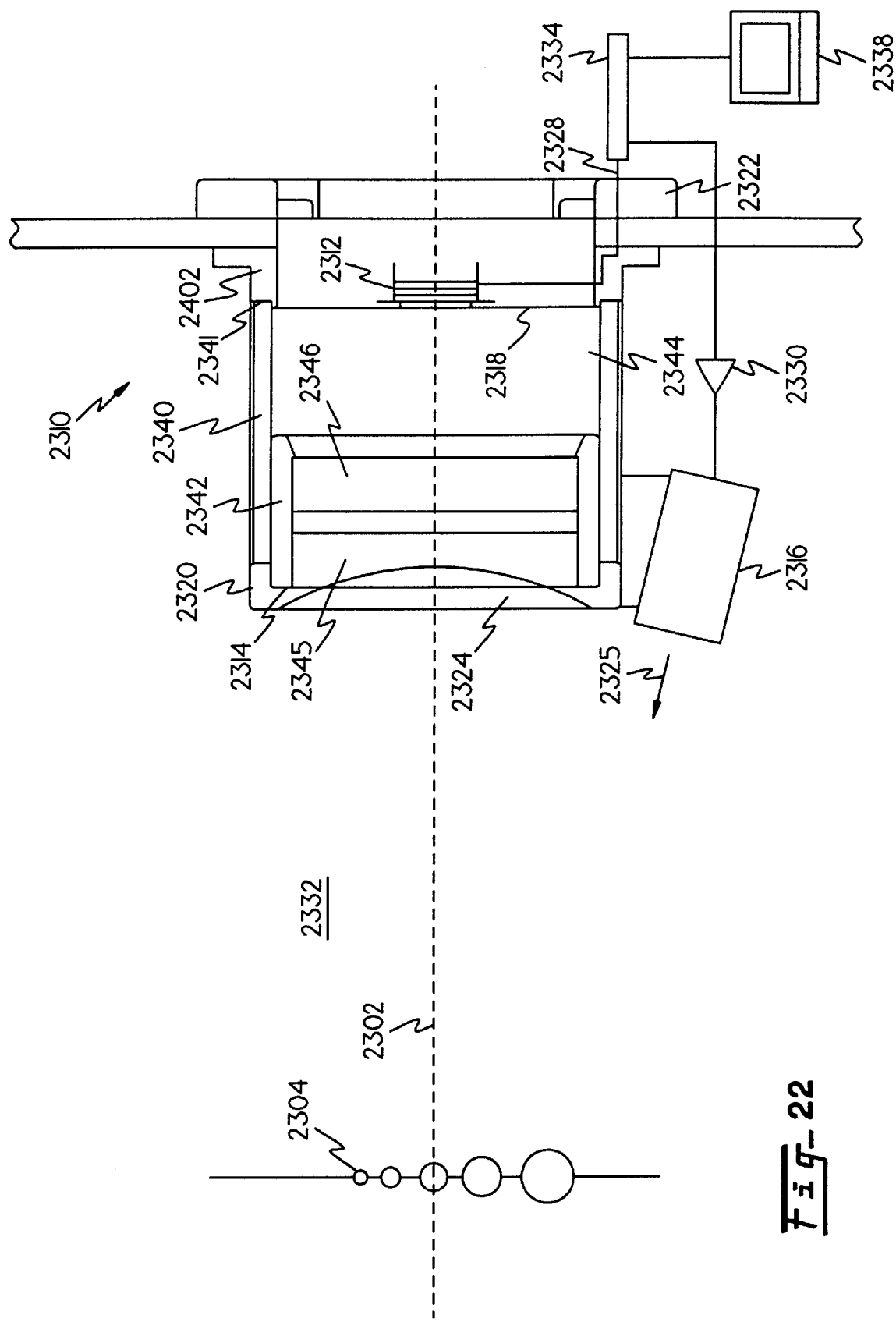
FIG. 22 shows the ultrasonic imaging system of the invention.

Refer now to FIG. 22 which shows one embodiment of the ultrasonic system 2310 of the invention. An object 2304 positioned at an object plane is insonified by an ultrasonic transmitter 2316. The transmitter transmits quasi incoherent ultrasound and is shown in more detail in FIG. 26. In one embodiment, the ultrasonic transmitter 2316 transmits ultrasonic energy with a wavelength of about 300 microns. Those skilled in the art will recognize that ultrasonic energy having various other wavelengths may be used without deviating from the spirit and scope of the invention. The object 2304 reflects the ultrasonic energy with varying degrees of effectiveness. Part of the reflected energy will fall on the ultrasonic lens system 2314. The ultrasonic lens 2314, positioned on ultrasonic axis 2302, receives the energy reflected from the object 2304 and transmits it to the ultrasonic array 2312.

Figure 23:
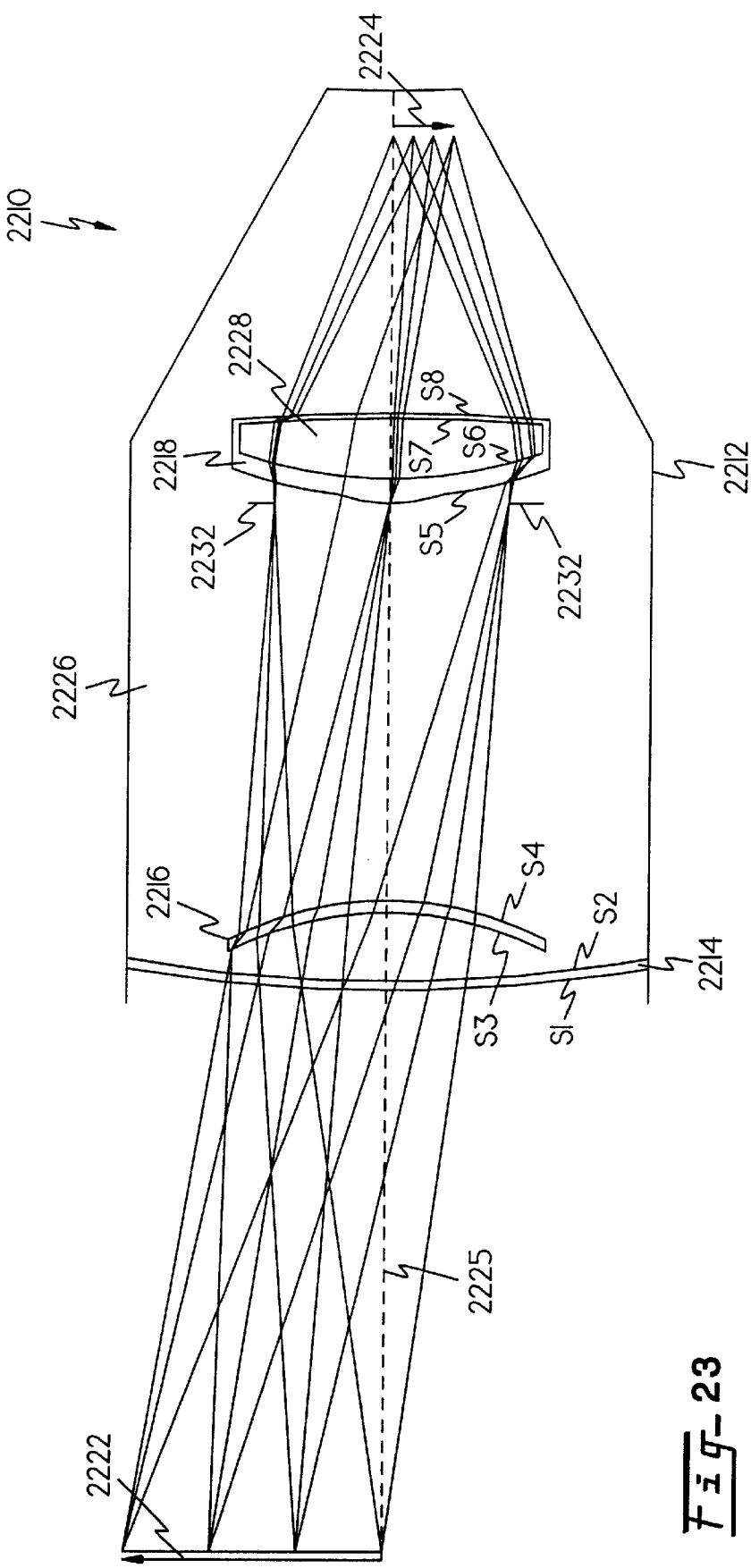
FIG. 23 shows the ultrasonic lens of the ultrasonic imaging system of FIG. 22.

The ultrasonic lens 2310 is constructed from a body 2320 and a lens system 324 that is shown in more detail in FIG. 23. The ultrasonic lens may be constructed using conventional lens making methods, including milling on a lathe, molding, injection molding, and other approaches to machining and chemical processing. The ultrasonic lens 2314 focuses the ultrasonic signal on the ultrasonic array 2312. The ultrasonic array is mounted behind a stretched membrane interface 2318. The stretched membrane interface 2318 is shown in more detail in FIG. 25. The ultrasonic array 2312 provides a two dimensional image of the object 2304 on image output line 2328. The two dimensional image is then processed with ultrasonic signal processing techniques described above.

In operation, the transmitter 2316, driven by a power amplifier 2330, sends a short pulse of ultrasonic energy into the fluid medium 2332 in the direction of arrow 2325. In one example, the fluid medium 2332 is water. The ultrasonic energy is then reflected off a target, such as object 2304, in the object plane of the ultrasonic lens system 2324, also known as an acoustical lens system 2324. The acoustical lens system 2324 focuses an image of the object 2304 onto the ultrasonic receiver array, also known as an acoustical focal plane array or a transducer hybrid assembly THA. The THA has a readout through additional electronics controller 2334 and a real time display is presented to the user on display device 2338. In one preferred embodiment, the acoustical focal plane array may be constructed following the methods described herein.

The ultrasonic camera 2310 housing 2340 encloses an ultrasonic medium 2344, such as water or other suitable ultrasonic transmission medium. A fluid tight lens housing 2342 contains similar ultrasonic medium 2345 and 2346. The fluid tight housing 2342 is attached to a mounting flange 2341 on a stretch membrane mount 2402.

Figure 30:
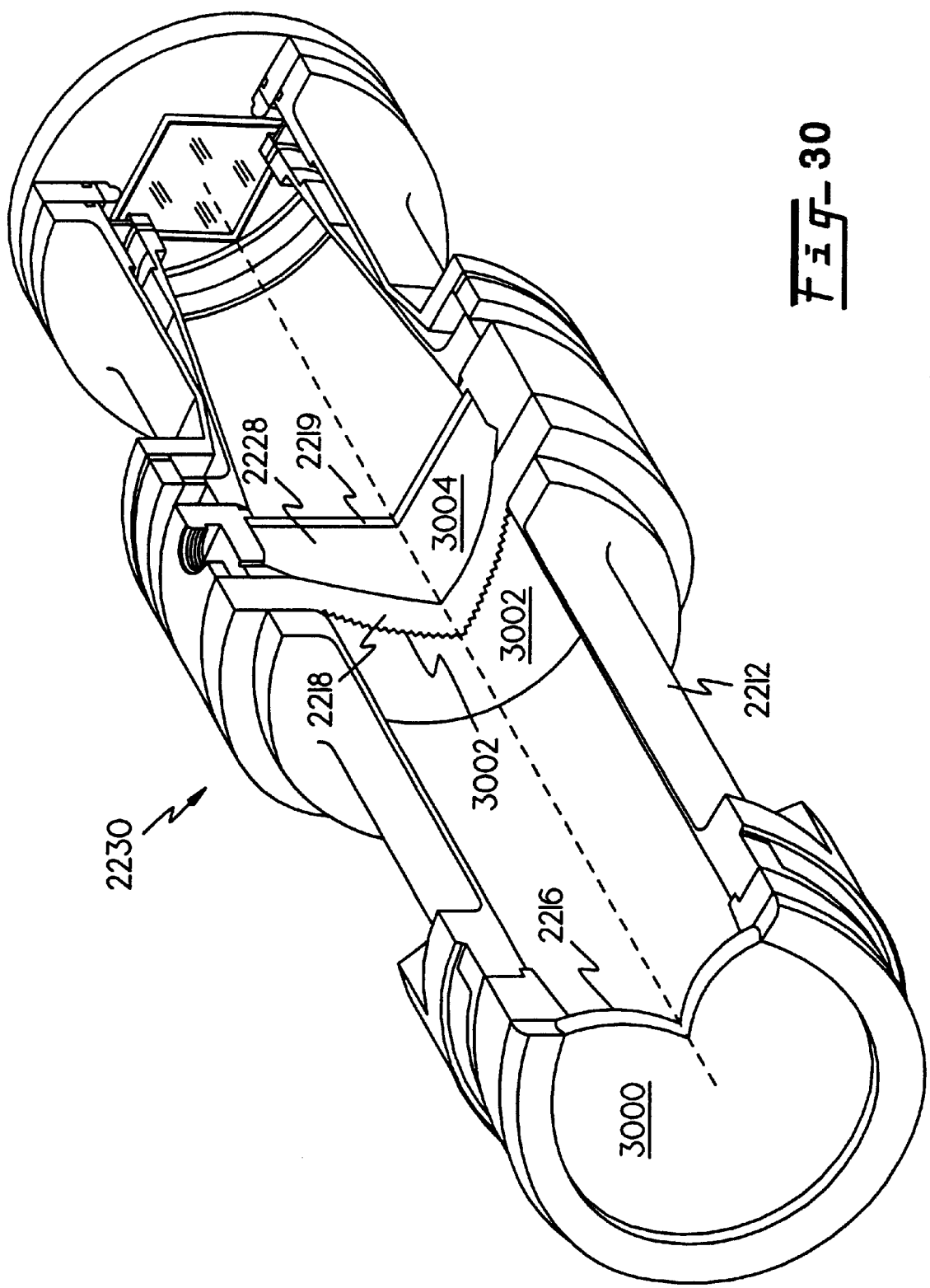
FIG. 30 shows an ultrasonic lens system for transmitting ultrasonic radiation at high efficiency with low aberration.

Refer now to FIG. 23 and FIG. 30 which show the ultrasonic lens system of the invention. The ultrasonic lens system 2230 is designed to operate with fewer elements and to efficiently transmit ultrasonic energy. The ultrasonic lens system 2210 comprises a housing 2212 that houses three ultrasonic elements, a ultrasonic lens window 2214, a polystyrene lens 2216 and a fluid filled polystyrene lens 2218. The fluid filled lens 2218 is shown as two lens 221 and 2219, in FIG. 30, held by housing 2212 with fluid 2228 between. An ultrasonic window 2214 is mounted to the housing 2212. Within the housing is an ultrasonic conductive material such as water 2226.

The window 2214 is slightly curved with a first surface S1 radius of about 646.56671 mm and a second surface S2 radius of about 830.829136 mm. The window is constructed from TPX, otherwise known as polymethylpentene. The window is provided for medical imaging applications to provide a standoff for the lens. The fluid material between the window and the first ultrasonic element creates the start of the ultrasonic path from the object. In the case of underwater, or under petroleum, applications, the window is not needed.

The next ultrasonic element in the lens system is a polystyrene lens 2216 that is located behind the window 2214. The polystyrene lens 2216 is 76.728 millimeters in diameter and is of an aspherical shape. The first surface S3 of the polystyrene lens 2216 has a radius of about −79.35737 mm. The second surface S4 of the polystyrene lens 2216 has a radius of about −162.88524 mm and an aspherical shape defined by the following equation:

$$Z = \frac{cx^2}{\left(1 + \sqrt{(1 - (1+k)c^2 x^2)}\right)} + Ax^4 + Bx^6 + Cx^8 + Dx^{10}$$

Where c=1/radius, radius=−162.88524 mm, K is the conic constant which is zero 0.0 in this case. A=−0.19759E-05, B=0.157598E-10, C=−0.201574E-12, and D=0.0. The equation defines a curve that is revolved around the ultrasonic axis 2225 to construct the ultrasonic lens shape.

The next ultrasonic element is a circular stop 2232 having an inside diameter of 63.657 mm and an outside diameter of 89.739 mm. The circular stop 2232 is positioned 89.028 mm from the polystyrene lens 2216.

The next ultrasonic element is a fluid filled compound lens 18 made of a fluid cavity 2228 in a polystyrene body 2218. The first aspheric surface S5 of the fluid filled compound lens 18 has a radius of about 54.76050 mm and an aspherical shape defined by equation 1. For this element, c=1/radius, radius=54.76050 mm, K is the conic constant which is zero 0.0 in this case, A=−0.433031E-05, B=−0.594032E-9, C=0.157306E-12, and D=−125397E-15. The equation defines a curve that is revolved around the ultrasonic axis 2225 to construct the lens shape. The second aspheric surface S6 of the polystyrene lens 2216 has a radius of about −89.89027 mm and an aspherical shape also defined by equation 1. For this element, c=1/radius, radius= 89.89027 mm, K is the conic constant which is zero 0.0 in this case, A=−0.679678E-06, B=0.463364E-11, C=0.146454E-13, and D=−0.179238E-17. The equation defines a curve that is also revolved around the ultrasonic axis 2225 to construct the lens shape. The fluid cavity is formed by a third surface S3 with a radius of about −578.81495 mm and a fourth surface S4 also with a radius of about −578.81495 mm. The fluid cavity is filled with FC40, a fluorocarbon fluid in which the velocity of sound is less than water and having a high density. Other fluids with a similar index of refraction may also be used.

The ultrasonic receiver transducer is shown at the focal point of the lens system 2210.

Refer now to FIG. 30 which shows an ultrasonic lens system 2230 may comprises a lens housing 2212 having a mount, and a plurality of ultrasonic elements 2216, 2218, 2219, attached to the mount, wherein the plurality of ultrasonic elements cooperate to transmit ultrasonic radiation at high efficiency with low aberration. High efficiency is achieved by surface treatments 3000, 3002, 3004 that adjust the acoustic impedance of the solid to the surrounding fluid. The surface treatments 3000, 3002, 3004 may comprise a single layer designed with a thickness of ¼ of a wavelength of sound and having an acoustical impedance equal to the square root of the product of the acoustic impedances of the lens and the fluid. Alternately, the surface treatment may comprise a composite layer comprised of multiple thicknesses of films which gradually shift the impedance from that of the fluid to that of the lens. In an alternate embodiment, the surface treatment is a surface finish that has a peak to valley distance and peak to peak distance of less than one wavelength. The surface finish is a pattern of grooves. The grooves are created with a lathe to construct concentric circles of V shape cuts. Multiple radial cuts create peaks along the surface of the lens. Those skilled in the art will recognize that other methods of creating peaks and valleys are within the scope of the invention and other manufacturing techniques may be used such as molding, injection molding, laser machining, and chemical processing. Alternately, the surface finish may be a random dimensional distribution of peaks. Alternately, the plurality of ultrasonic elements include one or more surfaces of diffractive ultrasonics. The diffractive surfaces are grooves with spatial relationships to effect a change in the peak of the ultrasonic staves.

In one embodiment of the invention, the ultrasonic transducer generates sound energy with about 300 micron wavelength.

Refer now to Table A which shows a listing of a CODE V run. CODE V is an optical design programing from Optical Research Associates, Inc. of Pasadena Calif. The ultrasound system of the invention has been modeled using the CODE V design package. Each surface of the system is modeled using a number of parameters. The model takes into account the radius of the surface relative to a point on the ultrasonic axis. The ultrasonic surface is assumed to be spherical unless otherwise specified. The material making up the surface is also specified.

TABLE A

```
CODE V > res budibox
    File BUDIBOX.LEN (24) has been restored
    with tolerances and sensitivity coefficients
CODE V > lis
              RDY               THI          RMD         GLA              CCY    THC    CLG
  > OBJ:      INFINITY          150.000098                                100    RED
     1:       646.56671         3.100000                  'TPX'           100    100
     2:       830.82936         12.400000                 AIR             100    100
     3:       −79.35737         3.720000                  'styrene'       21     100
     4:       −162.88524        89.020775                                 34     0
     ASP :
       K   :  0.000000      KC  :  100
       IC  :  YES           CUF :  0.000000        CCF  :  100
       A   :  −.197598E-05  B   :  0.157598E-10    C    :  −.201574E-12   D: 0.000000E+00
       AC  :  80            BC  :  81              CC   :  82             DC:      100
     STO :            INFINITY             0.000000                              100    COL
       6 :            54.76050             7.440000         'styrene'     67     COL
       ASP :
         K :  0.000000      KC  :  100
         IC :  YES          CUF :  0.000000        CCF  :  100
         A :  −.433031E-05  B   :  0.594032E-09    C    :  0.157306E-12   D :−.125397E-15
         AC :  90           BC  :  91              CC   :  92             DC: 93
       7 :            89.89027             16.6856285       'FC-40'       0      0
       ASP :
         K :  0.000000      KC  :  100
         IC :  YES          CUF :  0.000000        CCF  :  100
         A :  −.679678E-06  B   :  0.473364E-11    C    :  0.146454E-13   D :−.179238E-17
         AC :  0            BC  :  0               CC   :  0              DC: 0
     8 :      −578.81495           2.480000        'styrene'              13     100
     9 :      −578.81495           0.000000        'stuff'                100    100
     10 :     INFINITY             69.396383                              100    PIM
     IMG :    INFINITY             0.046822                               100    0
SPECIFICATION DATA:
    EPD    76.86552
    DIM         MM
```

TABLE A-continued

```
    WL      300000.00
    REF            1
    WTW            1
    XOB      0.00000      0.00000      0.00000      0.00000
    YOB      0.00000     20.00000     40.00000     56.60000
    VUX      0.00000      0.00699      0.02938      0.05924
    VLX      0.00000      0.00699      0.02938      0.05924
    VUY      0.00000      0.08451      0.20589      0.59048
    VLY      0.00000     -0.05673     -0.09289     -0.00216
APERTURE DATA/EDGE DEFINITIONS
    CA
    CIR S7                41.000000
    CIR S2   EDG          67.889504
PRIVATE CATALOG
    PWL          300000.00
    'FC72'            2.910000
    'stuff'           1.100000
    '1dpeth'          0.764000
    'bakelite'        0.937000
    'rtv511'          1.340000
    'TPX'             0.671000
    'styrene'         0.621000
    'FC-40'           2.345000
REFRACTIVE INDICES
    GLASS CODE      300000.00
    'TPX'             0.671000
    'styrene'         0.621000
    'FC-40'           2.345000
    'stuff'           1.100000
SOLVES
    RED     0.320000
    PIM
No pickups defined in system
INFINITE CONJUGATES
    EFL             71.6086
    BFL             46.4816
    FFL             73.7769
    FNO              0.9316
AT USED CONJUGATES
    RED              0.3200
    FNO              1.2300
    OBJ DIS        150.0001
    TT             354.2897
    IMG DIS         69.4432
    OAL            134.8464
    PARAXIAL IMAGE
        HT          18.1120
        THI         69.3964
        ANG         10.4895
    ENTRANCE PUPIL
        DIA         76.8655
        THI        142.9414
    EXIT PUPIL
        DIA         79.5818
        THI        -27.6575
```

Where:

EPC is the entrance pupil diameter,

WL is the wavelength,

REF is the reference surface,

WTW is the wavelength weight for multiple wavelengths,

XOB, YOB are the object height,

VUX, LX, VUY, VLY are vignetting factors,

CIR defines a circular aperture,

RED is the reduction ratio of the system,

EFL is the effective focal length,

BFL is the back focal length,

FFL is the front focal length,

FNO is the f number,

TT is the total track,

OAL is the object dispersion angle, and

ANG is the angle of the image to the center ray.

All indexes of refraction are computed relative to air to accomplish the ultrasonic simulation.

In operation, the lens system 2210 focuses energy reflected from an example object 2222 onto the image of an object 2224. The image of the object is detected by an ultrasonic transducer/receiver.

The images obtained by the lens system are enhanced by the interaction of the two main elements 2216 and 2218. Both elements work together to compensate for various aberrations, including spherical aberration, coma, astigmatism, and distortion. The system is designed to work at about 300 microns of ultrasonic signal and with a quasi acoustical source.

The ultrasonic camera may be made less costly and easier to manufacture since the ultrasonic camera requires relatively few parts. The ultrasonic camera is also more efficient because fewer elements absorb less energy. Fewer elements also reduce the amount of reflection, also improving the performance of the system.

Figure 24:
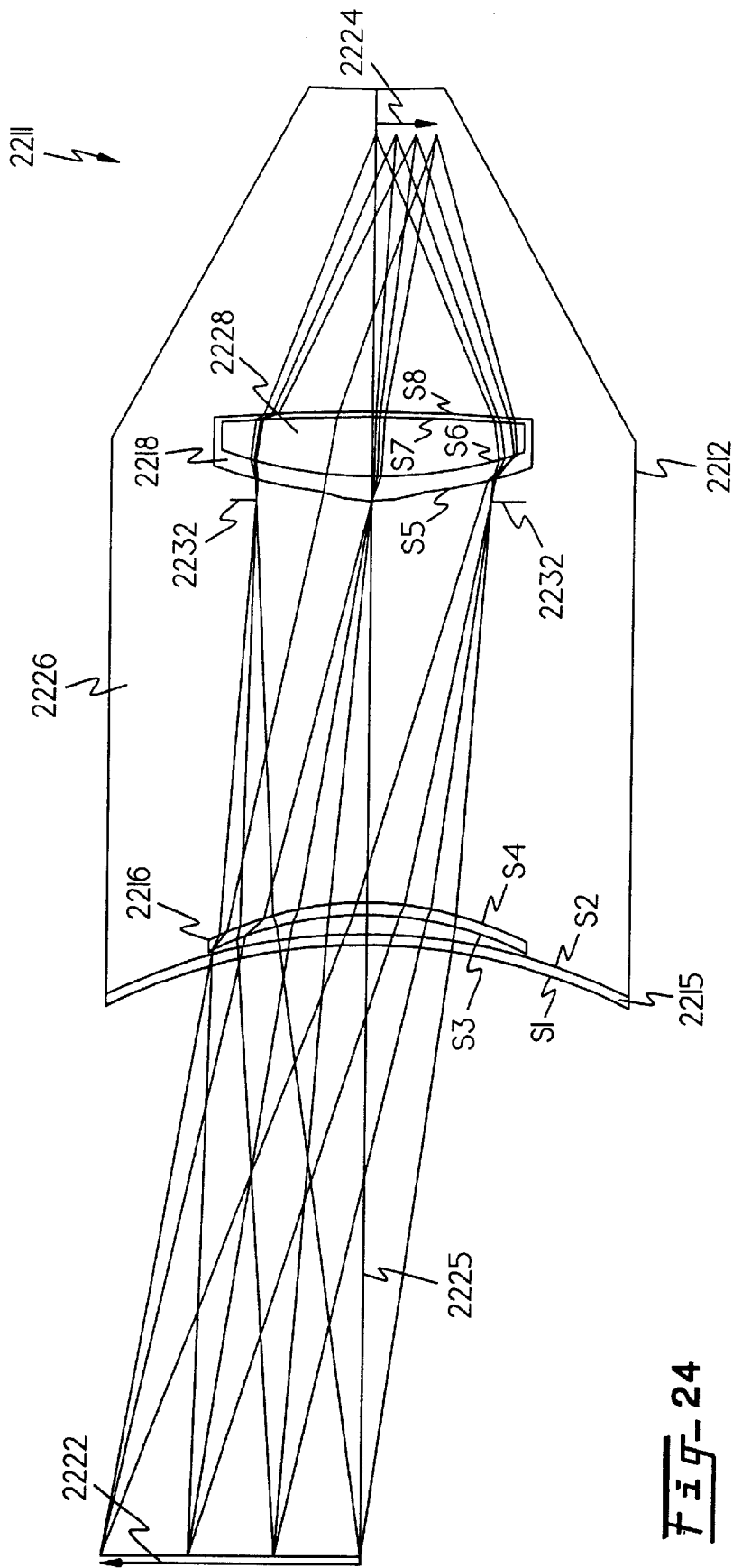
FIG. 24 shows an alternate lens of the ultrasonic imaging system of FIG. 22.

Refer now to FIG. 24 which shows an alternate embodiment of the ultrasonic lens 2211 of the invention. The ultrasonic lens 2211 is identical to ultrasonic lens 9210 shown in FIG. 23, except that the entrance window 2215 is shaped to better conform to certain anatomical features of the human body for mammography. FIG. 23 also illustrates the flexibility of the invention to be applied to differing ultrasonic environments. The entrance window 2215 can be further shaped to fit other anatomical features for both human and animal subjects.

The invention may be applied to underwater imaging environments such as mine detection. The invention may also be applied in petroleum environments for imaging in wells and drill holes.

Figure 25:
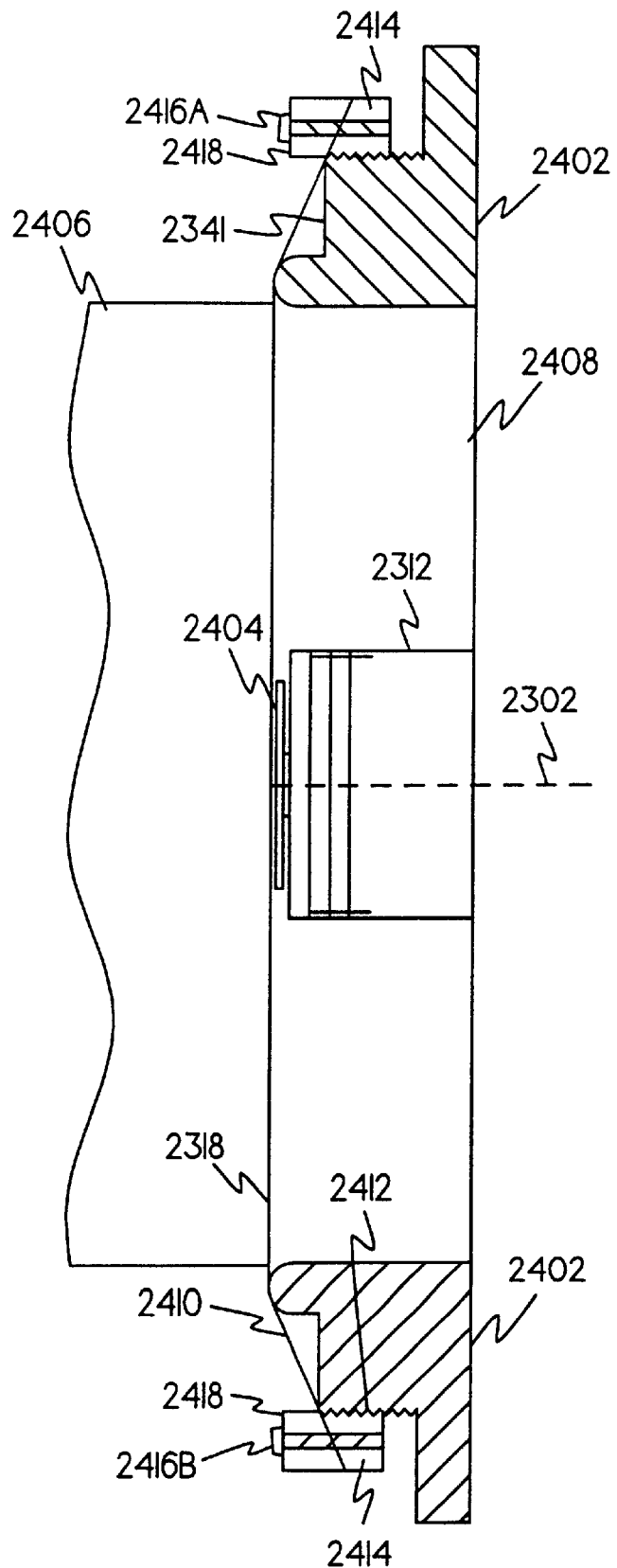
FIG. 25 shows a stretched membrane interface used in the ultrasonic imaging system of FIG. 22.

Refer now to FIG. 25 which shows one embodiment of the stretched membrane interface of the invention. The stretched membrane interface 2318 is stretched over mount 2402 and held taut to provide an air/water barrier. The membrane 2318 is coupled to the ultrasonic array 2312 with a film 2404 of coupling fluid such as oil. The ultrasonic array 2312 is positioned on the air side 2408 of the stretched membrane interface 2318. The water filled side 2406 faces the ultrasonic lens system 2324, shown in detail in FIG. 23. The use of water and the oil film provides a ultrasonically advantageous path for transmission of ultrasonic energy.

The membrane 2410 of the stretched membrane interface 2318 may be constructed from polymethylpentene also known as TPX, polyethylene or polyester. The membrane 2410 serves to hold the water on one side of the membrane 2410 and allows the ultrasonic array 2312 to be mounted on the air side. Those skilled in the art will appreciate that other suitable materials may be used. The material and thickness of the membrane may be selected for optimum sound transmission from the water 2406 into the ultrasonic array 2312. In an example embodiment of the invention, the membrane 2410 is made as thin as possible, i.e., less than 1/10 of a sound wavelength, in one example, about 30 microns.

In an alternate embodiment of the invention, the membrane 2410 is designed to make the acoustical impedance of the membrane 2410 equal to that of water. Acoustical impedance equals the velocity of sound times the density of the conduction medium. TPX is a good material to construct the membrane 2410 from because TPX has an impedance very close to water.

In another alternate embodiment of the invention, the membrane 2410 is designed with a thickness of ¼ of a wavelength of sound and designed to make the membrane's acoustical impedance equal to the sqrt($Z_{water} \times Z_{array}$). Where $Z_{water}$ is 1.5 Mrayls and $Z_{array}$ may be typically 20 Mrayls. This approach is analogous to the use of an antireflection coating on an optical lens.

The shape of the mount 2402 may be circular ring or similar shape that creates a membrane that is flat and taut then the membrane 2410 is stretched across it. The circular ring creates a flat, taut, drumhead shape.

The stretched membrane interface 23318 is fixed to the mount 2402 with a retaining ring 2412. The retaining ring 2412 has a first ring 2414 that encircles the mount 2402 and is threaded on an inside diameter to mate to threads on the mount 2402. A second ring 2418 also encircling the mount 2402 clamps the stretched membrane interface 2318 to the first ring 2414. The second ring 2418 is held to the first ring 2414 by a number of bolts placed around the circumference of the second ring 248 as exemplified by bolts 2416A and 2416B.

The oil film 2404 is used to couple the ultrasonic array 2312 to the membrane 2410. Ultrasound at certain frequencies does not transmit effectively through an air film, so that the coupling material is essential for the operation of the invention. The oil film should be as thin as possible, preferably less than 1/100 of the wavelength of the sound. The membrane 2318 forms an acoustic interface that conducts collected ultrasonic energy into the ultrasonic conduction medium 2406 and provides mechanical isolation of the transduction circuitry. The flat surface of the membrane 2318 provides a mechanical interface assuring, six dimensional (X, Y, Z, roll, pitch, yaw) alignment of the ultrasonic lens 2210 in relation to the transduction circuitry, ultrasonic array 2312. The opening through the mount 2402 provides unimpeded acoustical contact of the transduction means to the membrane.

The membrane provides for separating fluid in the collection apparatus from the transduction electrical circuitry, ultrasonic array 2312. The membrane further provides for ease of separation of the collection apparatus from the transduction apparatus, ultrasonic array 2312 and for impedance matching of the collection apparatus to the transduction apparatus. The membrane also provides transverse acoustical decoupling of the membrane from the transduction apparatus. Thus, the membrane reduces crosstalk between transducers.

In one embodiment, the oil film 2404 between the membrane 2318 and the transduction apparatus, ultrasonic array 2312 is less than 10% of a wavelength. In one embodiment, the oil film 2404 is a gel film.

Figure 26:
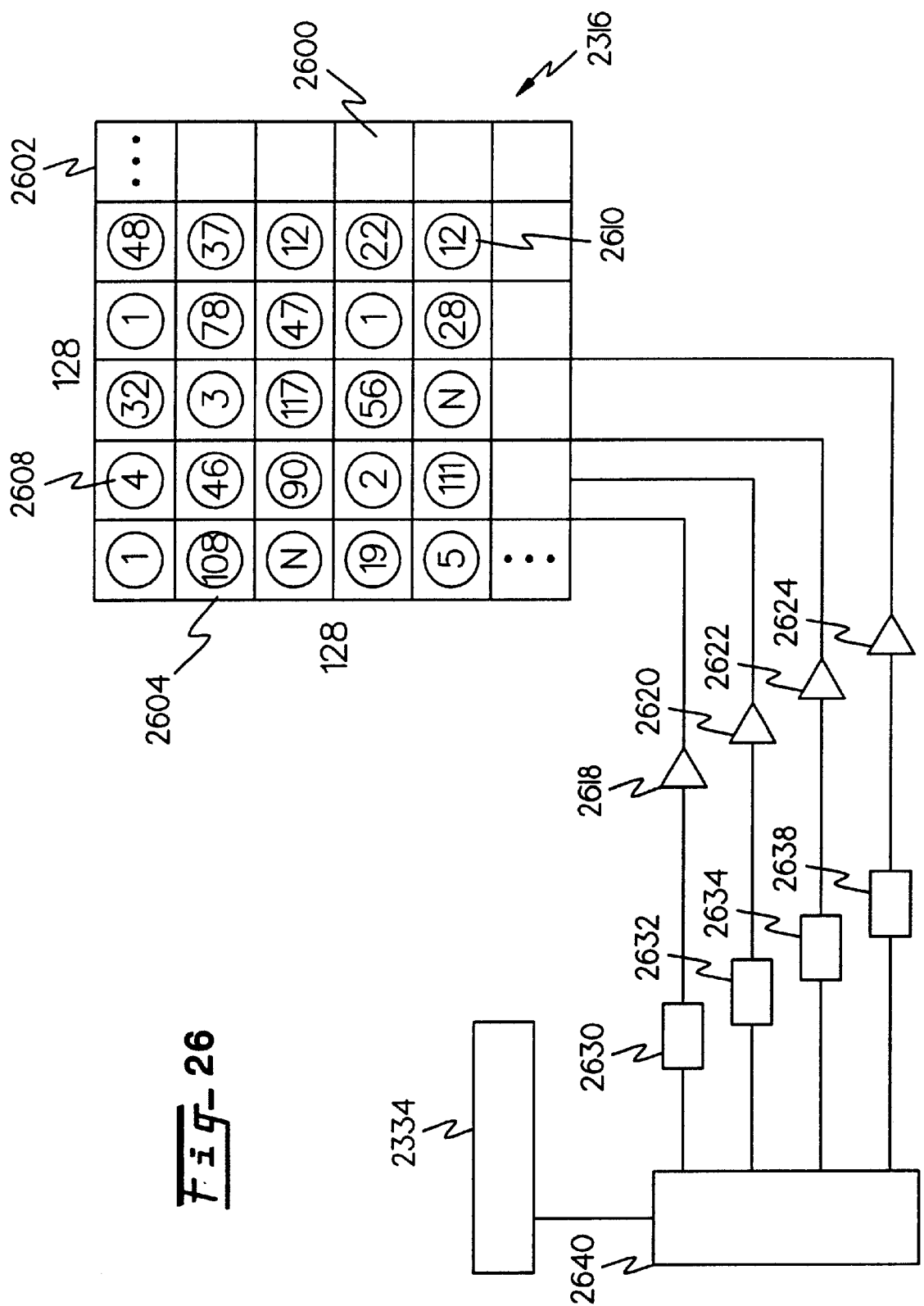
FIG. 26 shows an ultrasonic transmitter used in the ultrasonic imagine system of FIG. 22.

Refer now to FIG. 26 which shows one alternate of the ultrasonic transmitter of the invention. The ultrasonic transmitter 2316, in one embodiment, operates as a quasi incoherent acoustical source. A quasi incoherent acoustical source attempts to behave like a completely incoherent acoustical source, much like a white incandescent light bulb approximates an incoherent optical source. The ultrasonic transmitter 2316 provides a source of ultrasound that is both temporally incoherent as well as a spatially incoherent.

The benefit of an incoherent sound source for insonification of the object 2304 can be understood with an analogy to optical coherent imaging. When an object is insonified by a coherent optical source, such as a laser, the resulting picture or image appears speckled. This speckling makes the object difficult to view. When an object is insonified by a white light source, the images are clear and sharp. Similarly, with ultrasonic imaging a coherent source produces an analogous speckled ultrasonic image.

The invention achieves the quasi incoherent acoustical source by providing an array of ultrasonic transmitters with special design features. FIG. 26 shows the array 2600 having rows 2604 and columns 2608 of transmitters. Other configurations of the transmitters are possible, such as a linear configuration or a radial configuration. These configurations may comprise a rectangular pattern, a circular pattern, a reticulated pattern, a diagonal pattern, a grid pattern, a random pattern, a triangular pattern, a cross pattern or an oval pattern. Each transmitter is a member of a group of transmitters randomly distributed about the array. Each member of the group shares the property in that they have been tuned to the same resonant frequency. There are multiple groups, each group having a unique resonant frequency.

The resonant frequency may be changed by a number of approaches including attaching a predetermined mass to the transmitter. The extra mass attached to the ultrasonic transmitter changes its resonance frequency.

In one example embodiment, the array 2600 is broken into 128 groups wherein each group contains 128 transmitters distributed randomly around the array. Each group has a unique weighted mass made from gold, platinum or any other stable, easy to deposit or suitable metal attached to the transmitter to change its resonance frequency. This allows the transmitter to respond differently to an identical stimulus, providing, a quasi incoherence in the response. Each transmitter is designed to transmit in a range from approximately low ultrasound frequencies, such as 100 kHz, up to high ultrasound frequencies, such as 15 MHz.

In another example, the array contains 16 thousand transmitters. Each group in the array contains 100 transmitters, providing for 160 groups.

Each group is driven by a pulse driver such as an RF powered amplifier, shown for group 1 as amp 2618, for group 2 as amp 2620, for group 3 as amp 2622, and for group N as amp 2624. Each transmitter group is driven completely independently. The array 2600 further provides a temporal incoherence by varying the drive signal to each group with group driver controllers 2630, 2632, 2634 and 2638. Each group driver controller is interfaced to the ultrasonic camera controller 2334 by programmable interface 2640 that can change the drive signals to each group.

There are two types of drive signals that are contemplated by the invention. The first signal comprises a short tuned burst of a predetermined number of cycles of sine waves. A short burst of a sine wave is also known as a gated sine. In one example embodiment, group driver controller 2630 is programmed to generate a number of cycles of a sine wave, such as from two to three to up to five cycles. The frequency of the wave can vary from a nominal amount of one MHz, down to half a MHz, and up to two MHz.

The second type of drive signal is an impulse signal. When using the impulse, the group is driven by the impulse to have a random amount of waiting time varying from no wait to more than the period of the operating frequency of the array 2600. In an example embodiment, group driver 2638 stimulates driver 2624 with an impulse and waits a random amount of time before stimulating driver 2624 again. The overall array timing is controlled by programmable controller 2640 that is interfaced and controlled with the ultrasonic camera controller 2334. After the random wait time, another random group is stimulated with the same impulse. Both of these methods provide spatially and temporally incoherence insonification of the object 2304.

Other types of drive signals are contemplated by the invention, such as different wave shapes and stimulus duration, as well as different types of impulse, and impulse like drive signals.

Figure 27:
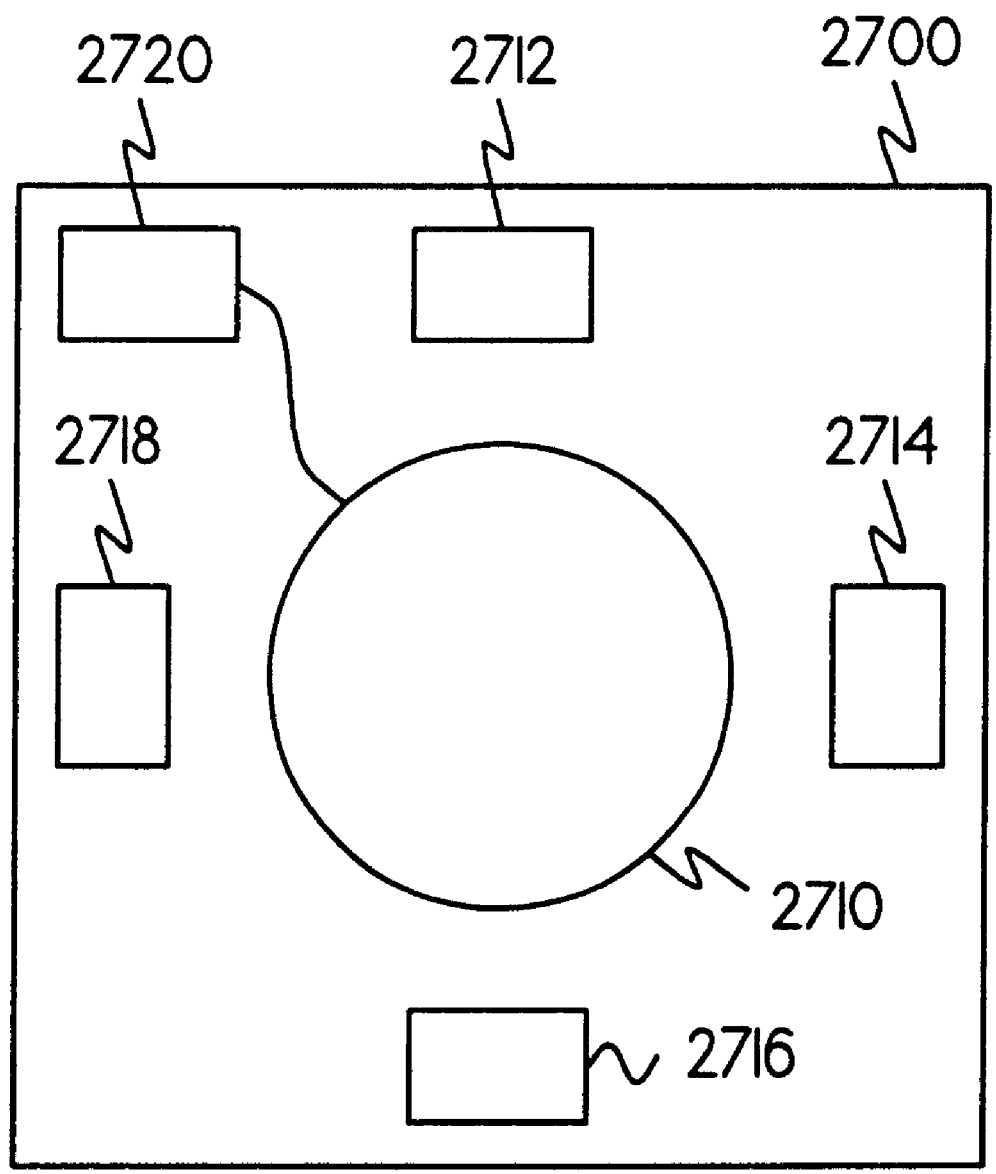
FIG. 27 shows an ultrasonic imaging system with an alternate ultrasonic transmitter system.

FIG. 27 shows an acoustical imaging system 2700 having an ultrasound camera 2710 connected to a signal processor 2720 with four acoustical transmitters 2712, 2714, 2716 and 2718. The ultrasound camera 2710 may be the ultrasonic camera shown in FIG. 22. Each transmitter has a principal axis of ultrasonic insonification. The quasi incoherent acoustical source can be approximated by using a multiple number of coherent acoustical sources that are varied in time and that acoustically illuminate the object at different principal angles of insonification. The ultrasonic sensor 2700 operates by transmitting a coherent beam from transmitter 2712 and taking a picture with the imager 2710. A second picture of the same scene is then taken with the imager 2710 insonified by a second source 2714. This process is repeated for source 2716 and 2718. The resulting four pictures are then added together to present a much smoother averaged image. The resulting image approximates one that would result from a system using a quasi incoherent acoustical source. The plurality of ultrasonic transmitters are driven sequentially to produce separate images of the object. The signal processor 2720 converts the sequential images to produce an image of the object of high quality by averaging two or more of the sequential images. In yet another alternate embodiment, a single ultrasonic transmitter may be sequentially moved to a new ankle of insonification. Alternatively, the multiple transmitter array may be electronically steered to a new angle of insonification. The electronic steering may be accomplished using conventional phase array techniques that alter the phase and timing of each element.

In one embodiment of the multiple transmitter array, groups of transmitters are constructed with different mechanical characteristics and are driven with the same signal. The different mechanical characteristics of the transmitter groups may be accomplished by designing the transmitter groups to have different resonance frequencies. Alternatively, different mechanical characteristics are achieved through different vertical spacings. The drive signal of the multiple transmitter array may comprise one or more electrical pulses. The electrical pulse may comprise an electrical sine wave burst, where frequency of the sine wave burst corresponds to the resonance frequency of each group of transmitters. Alternatively, the drive signal may comprise an electrical sine wave burst of a single frequency.

Figure 28:
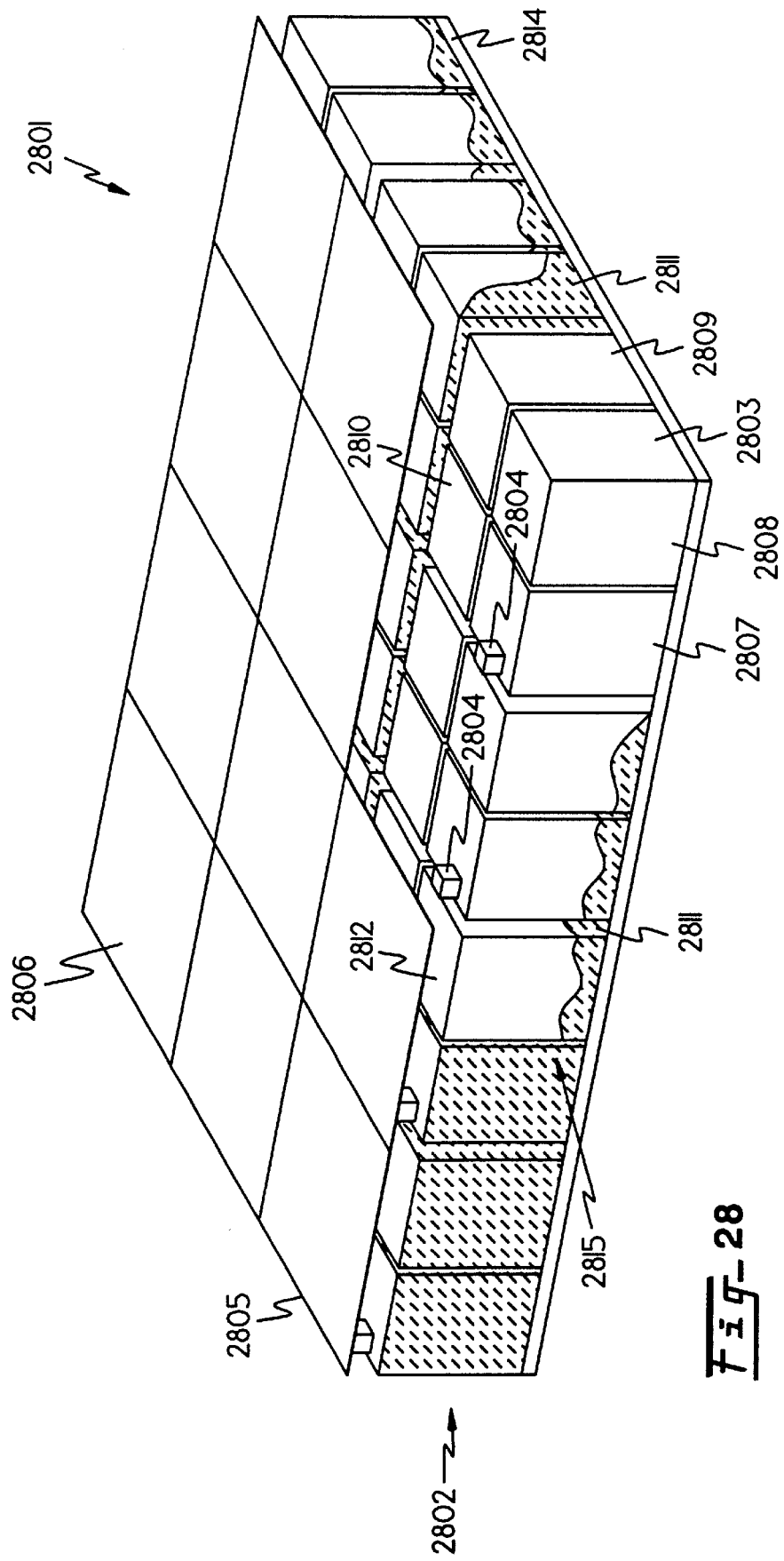
FIG. 28 shows an acoustical transducer hybrid array having an array of transducer elements.
Figure 29:
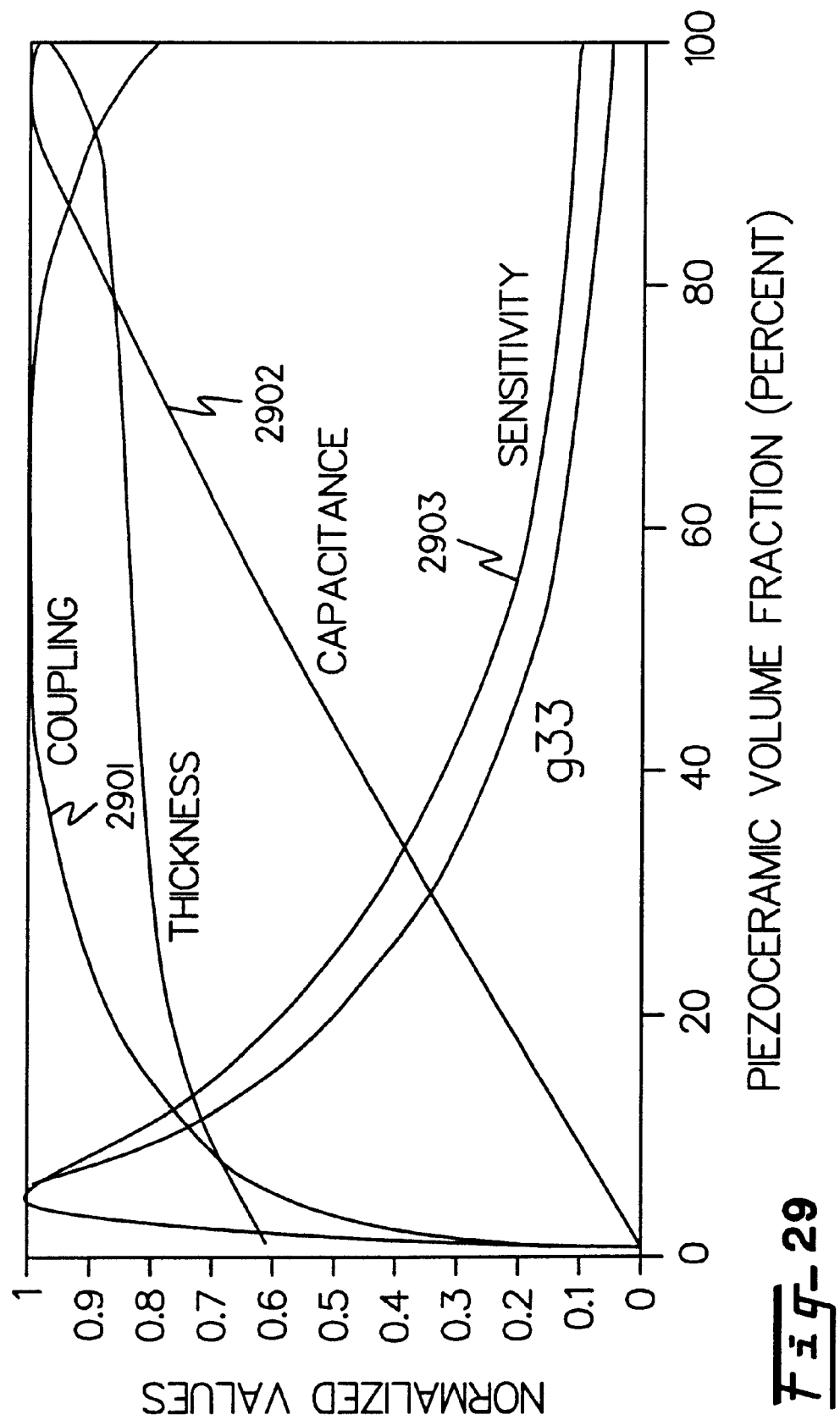
FIG. 29 plots the piezoelectric coupling co-efficient, capacitance and sensitivity at a constant resonance frequency as a function of piezoceramic volume fraction.

FIG. 28 shows an acoustical transducer hybrid array 2801 having an array 2802 of transducer elements 2803. Each transducer element 2803 uses a bump interconnection 2804 to connect to the silicon readout or transmit/readout integrated circuit 2805. The silicon readout or transmit/readout integrated circuit 2805 includes an electronic unit cell 2806 having a preamplifier connected to the bump interconnection 2804 as described above. The bump interconnection 2804 is connected to an individually isolated driving layer 2812. The bump interconnection 2804 has a predetermined size that is small relative to the size of the ultrasonic transducer. The individually isolated driving layer 2812 electrically connects the subelements and may be constructed of gold or other suitable conductor. Transducer 2803 is shown without the individually, isolated driving layer 2812 for clarity. The individually isolated driving layer 2812 is shown connecting the four subelements of transducer 2815. The silicon readout or transmit/readout integrated circuit 2804 also comprises signal processing and storage elements as described above. A common electrode 2814 electrically connects all transducer elements. Each transducer element 2803 is constructed of subelements 2807, 2808, 2809 and 2810. Each subelement may also be called a post. Each transducer element may be constructed from PZT-5H also known as lead zirconate titanate. Other suitable materials may also be used. In one example, the size of the transducer may be 0.2 millimeters by 0.2 millimeters. The space between the posts is filled with a filler such as epoxy DER332 from Dow Chemical Inc. In one embodiment, the epoxy 2811 may be a soft epoxy. The posts may be positioned at the corners of the transducer or anywhere in between. In an alternate preferred embodiment, the transducer element 2803 may have nine posts. The posts may also be round as well as square. The objective is to create posts with a high aspect ratio of height to width. The transducer element 2803 is said to have its volume fraction reduced by the division into four subelements. As shown in FIG. 29, the lower the volume fraction, the higher the ultrasonic sensitivity and the lower the capacitance of the transducer. The volume fraction is defined as the volume of the subelements divided by the volume of the subelements and the filler epoxy. In one example, the volume fraction may range from 10% to 50%. Conventional composite arrays are constructed with volume fractions of between 70% to 80%. The subelements may be constructed by sawing grooves in the ceramic, injection molding, chemical etching, laser ablation, and ion milling or other suitable method.

Conventional ultrasonic systems use micro-coaxial cable to connect the array to the front end electronics. Although micro-coax technology has improved dramatically in the past decade, interconnecting 16,384 array elements with separate wires remains a formidable challenge. In addition to this practical fabrication issue, the capacitance of a long coaxial cable (typically 40 pF/m) is much larger than that of a typical 2D array element (<1 pF). This creates a voltage divider that severely reduces the signal-to-noise ratio of the channel. The direct connection method using solder bumps 2804 reduces the interconnect length to less than 0.1 mm, reducing interconnection capacitance to a level where it is no longer a dominant factor in the channel signal-to-noise ratio.

The interconnection method is shown in FIG. 28. Solder bumps 2804 are deposited on both the array 2802 and the silicon integrated circuit 2805. During hybridization, the bumps 2804 are optically aligned and brought into contact to make an electrical connection. The contact area of the bumps on the array is approximately 20×20 microns, which provides adequate mechanical integrity, good electrical contact and has a minimal but not negligible, effect on the acoustics of an air-backed transducer design.

With this interconnection method, the input electronics has a capacitance of less than 100 fF. This provides a unique opportunity to optimize the composite piezoelectric material that is not available to conventional ultrasound systems. FIG. 29 plots the piezoelectric coupling co-efficient 2901, capacitance 2902 and sensitivity 2903 at a constant resonance frequency as a function of piezoceramic volume fraction as described by W. A. Smith and B. A. Auld in "Modeling 1–3 Composite Piezoelectrics: Thickness-Mode Oscillations," IEEE Trans. Ultrasonics Ferroelectrics and Frequency Control, UFFC-38: 40–47 (1991). By reducing the volume fraction of ceramic, sensitivity can be increased at the expense of lower capacitance while maintaining high coupling. This transducer hybrid assembly attains high efficiency by exploiting this phenomenon due to its particular structure.

The array may be configured to provide a quasi acoustical source as described above. The additional metal masses may be placed on top of the individually isolated driving layer 2812. Alternately an increase in mass may be accomplished by increasing the thickness of the individually isolated driving layer 2812. Alternately, the additional mass may be added by including additional metal to the common electrode end of the transducer 2814. In yet another embodiment, the lengths of the transducers may be varied to accomplish the variations in mass. Variations in length may be taken up by additional epoxy or the common electrode layer 2814.

The ultrasonic array 2312 may be operated in a send only mode or a send/receive mode utilizing the array 2801 of FIG. 28. In the send/receive mode the ultrasonic array 2312 provides the ultrasonic insonification. The array 2801 of FIG. 28 may be used in the transmitter 2316 of FIG. 22 and transmitters of FIG. 27 and as the array 2602 in FIG. 26. The invention provides a means for transducing the conducted electronic energy into electrical signals having a low volume fraction piezoelectric composite material in combination with a low capacitance electrical bump bond interconnection to a low stray capacitance preamplifier integrated circuit.

The invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An ultrasonic lens system comprising:

(a) an lens housing having a mount; and (b) a plurality of ultrasonic elements attached to the mount wherein the plurality of ultrasonic elements cooperate to transmit ultrasonic radiation at high efficiency with low aberration.

2. The apparatus of claim 1 wherein high efficiency is achieved by a surface treatment that adjusts the acoustic impedance of the ultrasonic elements to a surrounding fluid.

3. The apparatus of claim 2 wherein the surface treatment is a single layer designed with a thickness of ¼ of a wavelength of sound and with an acoustical impedance equal to the square root of the product of the acoustic impedances of the ultrasonic elements and the surrounding fluid.

4. The apparatus of claim 2 wherein the surface treatment is a composite layer comprised of multiple thicknesses of films that gradually shift an impedance from that of the surrounding fluid to that of the ultrasonic elements.

5. The apparatus of claim 2 wherein the surface treatment is a surface finish which has a peak to valley distance and peak to peak distance of less than one wavelength.

6. The apparatus of claim 5 wherein the surface finish is a pattern of grooves.

7. The apparatus of claim 5 wherein the surface finish is a random dimensional distribution of peaks.

8. The apparatus of claim 1 wherein the plurality of ultrasonic elements includes a surface of diffractive ultrasonics.

9. The apparatus of claim 8 wherein the surface of diffractive ultrasonics comprise grooves with spatial relationships to effect a change in the path of the ultrasonic waves.

10. The apparatus of claim 1 wherein the ultrasonic radiation has a wavelength of approximately 300 microns.

11. The ultrasonic lens system of claim 1 wherein the plurality of ultrasonic elements further comprise a first ultrasonic lens mounted to the mount having a first spherical surface and a first aspherical surface and a second ultrasonic lens mounted to the mount having a second aspherical surface, a third aspherical surface and a second spherical surface and a third spherical surface.

12. The apparatus of claim 11 wherein the first spherical surface has a first surface radius of about −79.35737 mm.

13. The apparatus of claim 11 wherein the first aspherical surface has a second surface radius of about −162.88524 mm and the first aspherical surface is defined by the equation:

$$Z = \frac{cx^2}{\left(1 + \sqrt{(1-(1+k)c^2x^2)}\right)} + Ax^4 + Bx^6 + Cx^8 + Dx^{10}$$

where c=1/radius, radius=54.76050 mm, K is the conic constant which is zero 0.0 in this case, A=−0.433031E-05, B=0.594032E-9, C=0.157306E-12, and D=−125397E-15.

14. The apparatus of claim 11 wherein the second aspherical surface has a third surface radius of about 54.76050 mm and the second aspherical surface is defined by the equation:

$$Z = \frac{cx^2}{\left(1 + \sqrt{(1-(1+k)c^2x^2)}\right)} + Ax^4 + Bx^6 + Cx^8 + Dx^{10}$$

where c=1/radius, radius=89.89027 mm, K is the conic constant which is zero 0.0 in this case, A=−0.679678E-06, B=0.463364E-11, C=0.146454E-13, and D=−0.17928E-17.

15. The apparatus of claim 11 wherein the third aspherical surface has a fourth surface radius of about 89.89027 mm and the third aspherical surface is defined by the equation:

$$Z = \frac{cx^2}{\left(1 + \sqrt{(1-(1+k)c^2x^2)}\right)} + Ax^4 + Bx^6 + Cx^8 + Dx^{10}$$

where c=1/radius, radius=89.89027 mm, K is the conic constant which is zero 0.0 in this case, A=−0.679678E-06, B=0.473364E-11, C=0.146454E-13, and D=0.179238E-17.

16. The apparatus of claim 11 wherein the second spherical surface has a fifth surface radius of about −578.81495 mm.

17. The apparatus of claim 11 Wherein the third spherical surface has a sixth surface radius of about −578.81495 mm.

18. The apparatus of claim 11 wherein the first ultrasonic lens is made from polystyrene.

19. The apparatus of claim 11 wherein the second ultrasonic lens is a liquid filled polystyrene lens.

20. The apparatus of claim 19 wherein a liquid in the liquid filled polystyrene lens is FC40.

21. The apparatus of claim 1 wherein the lens housing is filled with water.

22. An ultrasonic lens system comprising:
(a) a first ultrasonic lens made from polystyrene having a first radius of curvature of about −79.35737 mm, and a second radius of curvature of about −162.88524 mm, with an aspherical surface defined by the equation:

$$Z = \frac{cx^2}{\left(1 + \sqrt{(1-(1+k)c^2x^2)}\right)} + Ax^4 + Bx^6 + Cx^8 + Dx^{10}$$

where c=1/radius, radius=54.76050 mm, K is the conic constant which is zero 0.0 in this case, A=−0.433031E-05, B=0.594032E-9, C=0.157306E-12, and D=−125397E-15, and a first thickness through the ultrasonic center of 3.72 mm; and (b) a second fluid filed ultrasonic lens made from polystyrene having a third radius of curvature of about 54.76050 mm with a second aspherical surface defined by the equation:

$$Z = \frac{cx^2}{\left(1 + \sqrt{(1-(1+k)c^2x^2)}\right)} + Ax^4 + Bx^6 + Cx^8 + Dx^{10}$$

where c=1/radius, radius=89.89027 mm, K is the conic constant which is zero 0.0 in this case, A=−0.679678E-06, B=0.463364E-11, C=0.146454E-13, and D=−0.179238E-17, a third aspherical surface with a fourth radius of curvature of 89.89027 mm having a fourth aspherical surface defined by the equation:

$$Z = \frac{cx^2}{\left(1 + \sqrt{(1-(1+k)c^2x^2)}\right)} + Ax^4 + Bx^6 + Cx^8 + Dx^{10}$$

where c=1/radius, radius=89.89027 mm, K is the conic constant which is zero 0.0 in this case, A='0.679678E-06, B=0.473364E-11, C=0.146454E-13, and D=0.179238E-17, and a second thickness through the ultrasonic center of 7.44 mm, a fifth radius of curvature of about −578.81495 mm located about 89.028 mm from the fourth radius, and a sixth radius of curvature of about −578.81495 mm with a third thickness through the ultrasonic center of 2.48 mm.

* * * * *

UNITED STATES PATENT AND TRADEMARK OFFICE
CERTIFICATE OF CORRECTION

PATENT NO.     : 6,325,757 B1
DATED          : December 4, 2001
INVENTOR(S)    : Erikson et al.

It is certified that error appears in the above-identified patent and that said Letters Patent is hereby corrected as shown below:

Column 1,
Line 21, delete the word "pool" and insert the word -- poor --.
Line 34, delete the word "Once" and insert the word -- One --.

Column 2,
Line 9, delete the word "wraith" and replace it with the word -- with --.
Line 35, delete the ",".

Column 3,
Line 2, delete the word "within" and replace it with -- with --.

Column 5,
Line 23, delete the year "1999" and replace it with the year -- 1991 --.

Column 6,
Line 15, delete the word "arrays" and replace it with the word -- array --.
Line 18, delete the number "16" and replace it with the number -- 156 --.

Column 8,
Line 8, delete the word "re-radiate" and replace it with the word -- re-radiated --.
Line 45, delete the number "1226" and replace it with the numbers -- 1 226 --.
Line 47, delete the number "2228" and replace it with the numbers -- 2 228 --.

Column 9,
Line 3, delete the word "bias" and replace it with the word -- was --.
Line 10, after the word "Systems" delete the "." and replace it with -- , --.
Line 29, delete the word "any" and replace it with the word -- array --.

Column 10,
Line 3, delete the number "476" and replace it with the number -- 426 --.
Line 29, delete the word "around" and insert the word -- ground --.
Line 32, delete the words "pulse, in" and replace with the words -- pulse. In --.

Column 11,
Line 28, delete the word "on-clip" and replace it with the word -- on-chip --.
Line 28, delete the ",". (two occurrences)
Line 53, delete the number "324" and replace it with the number -- 2324 --.

UNITED STATES PATENT AND TRADEMARK OFFICE
CERTIFICATE OF CORRECTION

PATENT NO. : 6,325,757 B1
DATED : December 4, 2001
INVENTOR(S) : Erikson et al.

It is certified that error appears in the above-identified patent and that said Letters Patent is hereby corrected as shown below:

Column 12,
Line 27, delete the number "221" and replace it with the number -- 2221 --.
Line 34, delete the number "830.829136" and replace it with the number
-- 830.82936 --.

Column 13,
Line 24, delete the word "may".

Column 14,
Line 21, delete the word "staves" and replace it with the word -- waves --.
Line 26, delete the word "programing" and replace it with the word -- program --.

Column 17,
Line 3, delete the number "9210" and replace it with the number -- 2210 --.
Line 49, delete the subscript word "$_{is}$" and replace it with the regular script word
-- is --.
Line 54, delete the word "then" and replace it with the word -- when --.
Line 56, delete the number "23318" and replace it with the number -- 2318 --.

Column 19,
Line 6, delete the second ",".

Column 20,
Line 6, delete the word "ankle" and replace it with the word -- angle --.
Line 39, delete ",".
Line 53, delete the number "2811".
Line 54, after the word "epoxy" insert the number -- 2811 --.

Column 21,
Line 25, after the word "minimal" insert a -- , --.

UNITED STATES PATENT AND TRADEMARK OFFICE
CERTIFICATE OF CORRECTION

PATENT NO.   : 6,325,757 B1
DATED        : December 4, 2001
INVENTOR(S)  : Erikson et al.

It is certified that error appears in the above-identified patent and that said Letters Patent is hereby corrected as shown below:

Column 23,
Line 13, delete the number "0.17928E-17" and replace it with the number -- 0.179238E-17 --.
Line 30, delete the word "Wherein" and replace it with the word -- wherein --.

Column 24,
Line 35, delete the " ' " and replace it with the negative sign -- - --.

Signed and Sealed this

Twelfth Day of November, 2002

Attest:

JAMES E. ROGAN
Attesting Officer
Director of the United States Patent and Trademark Office